(12) United States Patent
Lakin et al.

(10) Patent No.: US 7,840,256 B2
(45) Date of Patent: Nov. 23, 2010

(54) IMAGE GUIDED TRACKING ARRAY AND METHOD

(75) Inventors: Ryan Cameron Lakin, Warsaw, IN (US); Ryan Schoenefeld, Fort Wayne, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 1076 days.

(21) Appl. No.: 11/299,886

(22) Filed: Dec. 12, 2005

(65) Prior Publication Data

US 2007/0016009 A1    Jan. 18, 2007

Related U.S. Application Data

(60) Provisional application No. 60/694,178, filed on Jun. 27, 2005.

(51) Int. Cl.
*A61B 5/05* (2006.01)
(52) U.S. Cl. .................. 600/426; 600/423; 600/424; 600/414; 600/421; 408/158; 408/147
(58) Field of Classification Search ......... 600/407–480; 408/158, 147
See application file for complete search history.

(56) References Cited

U.S. PATENT DOCUMENTS

| | | |
|---|---|---|
| 4,341,220 A | 7/1982 | Perry |
| 4,360,028 A | 11/1982 | Barbier et al. |
| 4,583,538 A | 4/1986 | Onik et al. |
| 4,791,934 A | 12/1988 | Brunnett |
| 4,945,914 A | 8/1990 | Allen |
| 4,991,579 A | 2/1991 | Allen |
| 5,016,639 A | 5/1991 | Allen |

(Continued)

FOREIGN PATENT DOCUMENTS

EP    0 427 358 A1    5/1991

(Continued)

OTHER PUBLICATIONS

Muller PE, Pellengahr C, Witt M, Kircher J, Refior HJ, Jansson V. Influence of minimally invasive surgery on implant positioning and the functional outcome for medial unicompartmental knee arthroplasty. J Arthroplasty 2004; 19(3): 296-301.

(Continued)

*Primary Examiner*—Long V Le
*Assistant Examiner*—Joel F Brutus
(74) *Attorney, Agent, or Firm*—Taft, Stettinius & Hollister LLP

(57) ABSTRACT

An array for use with a surgical navigation system is provided. The array comprises a frame and first, second and third markers attached to the frame. The first, second and third markers are detectable by a tracking system used in image guided surgery, and the first marker is movable relative to the frame. In one embodiment, at least one marker slides along the frame from a first position where it is held in place to a second position where it is also held in place. In another embodiment, one or more of the markers is removed from the frame at a first position and reattached to the frame at a second position. In still another embodiment, a portion of the frame itself moves with the movable marker.

11 Claims, 22 Drawing Sheets

U.S. PATENT DOCUMENTS

| | | | |
|---|---|---|---|
| 5,086,401 A | 2/1992 | Glassman et al. | |
| 5,094,241 A | 3/1992 | Allen | |
| 5,097,839 A | 3/1992 | Allen | |
| 5,119,817 A | 6/1992 | Allen | |
| 5,142,930 A | 9/1992 | Allen et al. | |
| 5,178,164 A | 1/1993 | Allen | |
| 5,211,164 A | 5/1993 | Allen | |
| 5,222,499 A | 6/1993 | Allen et al. | |
| 5,230,338 A | 7/1993 | Allen et al. | |
| 5,309,913 A | 5/1994 | Kormos et al. | |
| 5,383,454 A | 1/1995 | Bucholz | |
| 5,389,101 A | 2/1995 | Heilbrun et al. | |
| 5,397,329 A | 3/1995 | Allen | |
| 5,517,990 A | 5/1996 | Kalfas et al. | |
| 5,603,318 A | 2/1997 | Heilbrun et al. | |
| 5,628,315 A | 5/1997 | Vilsmeier et al. | |
| 5,682,886 A | 11/1997 | Delp et al. | |
| 5,682,890 A | 11/1997 | Kormos et al. | |
| D387,427 S | 12/1997 | Bucholz et al. | |
| 5,732,703 A | 3/1998 | Kalfas et al. | |
| 5,769,861 A | 6/1998 | Vilsmeier | |
| 5,772,594 A | 6/1998 | Barrick | |
| 5,776,064 A | 7/1998 | Kalfas et al. | |
| 5,799,055 A | 8/1998 | Peshkin et al. | |
| 5,836,954 A | 11/1998 | Heilbrun et al. | |
| 5,851,183 A | 12/1998 | Bucholz | |
| 5,871,018 A | 2/1999 | Delp et al. | |
| 5,891,034 A | 4/1999 | Bucholz | |
| 5,902,239 A | 5/1999 | Buurman | |
| 5,967,982 A | 10/1999 | Barnett | |
| 5,980,535 A | 11/1999 | Barnett et al. | |
| 5,987,960 A | 11/1999 | Messner et al. | |
| 5,999,837 A | 12/1999 | Messner et al. | |
| D420,132 S | 2/2000 | Bucholz et al. | |
| 6,021,343 A | 2/2000 | Foley et al. | |
| D422,706 S | 4/2000 | Bucholz et al. | |
| 6,050,724 A | 4/2000 | Schmitz et al. | |
| 6,069,932 A | 5/2000 | Peshkin et al. | |
| 6,096,050 A | 8/2000 | Audette | |
| 6,122,541 A | 9/2000 | Cosman et al. | |
| 6,161,033 A | 12/2000 | Kuhn | |
| 6,167,145 A | 12/2000 | Foley et al. | |
| 6,167,292 A | 12/2000 | Badano et al. | |
| 6,178,345 B1 | 1/2001 | Vilsmeier et al. | |
| 6,187,018 B1 | 2/2001 | Sanjay-Gopal et al. | |
| 6,190,395 B1 | 2/2001 | Williams | |
| 6,198,794 B1 | 3/2001 | Peshkin et al. | |
| 6,205,411 B1 | 3/2001 | DiGioia, III et al. | |
| 6,235,038 B1 | 5/2001 | Hunter et al. | |
| 6,236,875 B1 | 5/2001 | Bucholz et al. | |
| 6,246,900 B1 | 6/2001 | Cosman et al. | |
| 6,285,902 B1 | 9/2001 | Kienzle, III et al. | |
| 6,306,126 B1 | 10/2001 | Moctezuma | |
| 6,351,659 B1 * | 2/2002 | Vilsmeier | 600/407 |
| 6,377,839 B1 | 4/2002 | Kalfas et al. | |
| 6,379,302 B1 | 4/2002 | Kessman et al. | |
| 6,381,485 B1 | 4/2002 | Hunter et al. | |
| 6,402,762 B2 | 6/2002 | Hunter et al. | |
| 6,424,856 B1 | 7/2002 | Vilsmeier et al. | |
| 6,428,547 B1 | 8/2002 | Vilsmeier et al. | |
| 6,434,415 B1 | 8/2002 | Foley et al. | |
| 6,434,507 B1 | 8/2002 | Clayton et al. | |
| 6,470,207 B1 | 10/2002 | Simon et al. | |
| 6,477,400 B1 | 11/2002 | Barrick | |
| 6,484,049 B1 * | 11/2002 | Seeley et al. | 600/426 |
| 6,490,467 B1 * | 12/2002 | Bucholz et al. | 600/407 |
| 6,490,475 B1 | 12/2002 | Seeley et al. | |
| 6,490,777 B1 | 12/2002 | Proulx et al. | |
| 6,491,699 B1 | 12/2002 | Henderson et al. | |
| 6,493,574 B1 | 12/2002 | Ehnholm et al. | |
| 6,507,751 B2 | 1/2003 | Blume et al. | |
| 6,527,443 B1 | 3/2003 | Vilsmeier et al. | |
| 6,535,756 B1 | 3/2003 | Simon et al. | |
| 6,551,325 B2 | 4/2003 | Neubauer et al. | |
| 6,553,152 B1 | 4/2003 | Miller et al. | |
| 6,556,857 B1 | 4/2003 | Estes et al. | |
| 6,584,174 B2 | 6/2003 | Schubert et al. | |
| 6,609,022 B2 | 8/2003 | Vilsmeier et al. | |
| 6,674,916 B1 | 1/2004 | Deman et al. | |
| 6,684,098 B2 * | 1/2004 | Oshio et al. | 600/429 |
| 6,697,664 B2 | 2/2004 | Kienzle, III et al. | |
| 6,714,629 B2 | 3/2004 | Vilsmeier | |
| 6,724,922 B1 | 4/2004 | Vilsmeier | |
| 6,725,080 B2 | 4/2004 | Melkent et al. | |
| 6,725,082 B2 | 4/2004 | Sati et al. | |
| 6,754,374 B1 | 6/2004 | Miller et al. | |
| 6,772,002 B2 | 8/2004 | Schmidt et al. | |
| 6,776,526 B2 | 8/2004 | Zeiss | |
| 6,782,287 B2 | 8/2004 | Grzeszczuk et al. | |
| 6,856,826 B2 | 2/2005 | Seeley et al. | |
| 6,856,827 B2 | 2/2005 | Seeley et al. | |
| 6,856,828 B2 | 2/2005 | Cossette et al. | |
| 6,887,245 B2 | 5/2005 | Kienzle, III et al. | |
| 6,887,247 B1 | 5/2005 | Couture et al. | |
| 6,892,088 B2 | 5/2005 | Faulkner et al. | |
| 6,895,268 B1 | 5/2005 | Rahn et al. | |
| 6,896,657 B2 | 5/2005 | Willis | |
| 6,917,827 B2 | 7/2005 | Kienzle, III | |
| 6,920,347 B2 | 7/2005 | Simon et al. | |
| 6,925,339 B2 | 8/2005 | Grimm et al. | |
| 6,926,673 B2 | 8/2005 | Roberts et al. | |
| 6,932,823 B2 | 8/2005 | Grimm et al. | |
| 6,947,582 B1 | 9/2005 | Vilsmeier et al. | |
| 6,947,783 B2 | 9/2005 | Immerz | |
| 6,950,689 B1 | 9/2005 | Willis et al. | |
| 6,978,166 B2 | 12/2005 | Foley et al. | |
| 6,988,009 B2 | 1/2006 | Grimm et al. | |
| 6,990,220 B2 | 1/2006 | Ellis et al. | |
| 7,008,430 B2 | 3/2006 | Dong et al. | |
| 7,010,095 B2 | 3/2006 | Mitschke et al. | |
| 7,346,417 B2 * | 3/2008 | Luth et al. | 700/117 |
| 2001/0007918 A1 | 7/2001 | Vilsmeier et al. | |
| 2001/0011175 A1 | 8/2001 | Hunter et al. | |
| 2001/0027271 A1 | 10/2001 | Franck et al. | |
| 2001/0036245 A1 | 11/2001 | Kienzle, III et al. | |
| 2001/0051881 A1 | 12/2001 | Filler | |
| 2002/0077540 A1 | 6/2002 | Kienzle, III | |
| 2002/0077543 A1 * | 6/2002 | Grzeszczuk et al. | 600/424 |
| 2002/0095081 A1 | 7/2002 | Vilsmeier | |
| 2002/0151894 A1 | 10/2002 | Melkent et al. | |
| 2002/0183610 A1 | 12/2002 | Foley et al. | |
| 2002/0188194 A1 | 12/2002 | Cosman | |
| 2003/0059097 A1 | 3/2003 | Abovitz et al. | |
| 2003/0209096 A1 | 11/2003 | Pandey et al. | |
| 2004/0015077 A1 | 1/2004 | Sati et al. | |
| 2004/0030245 A1 | 2/2004 | Noble et al. | |
| 2004/0073228 A1 | 4/2004 | Kienzle, III et al. | |
| 2004/0087852 A1 | 5/2004 | Chen et al. | |
| 2004/0097952 A1 | 5/2004 | Sarin et al. | |
| 2004/0106861 A1 * | 6/2004 | Leitner | 600/407 |
| 2004/0127788 A1 | 7/2004 | Arata | |
| 2004/0169673 A1 | 9/2004 | Crampe et al. | |
| 2004/0254454 A1 | 12/2004 | Kockro | |
| 2004/0267242 A1 | 12/2004 | Grimm et al. | |
| 2005/0015003 A1 | 1/2005 | Lachner et al. | |
| 2005/0015005 A1 | 1/2005 | Kockro | |
| 2005/0015022 A1 | 1/2005 | Richard et al. | |
| 2005/0015099 A1 | 1/2005 | Momoi et al. | |
| 2005/0020909 A1 | 1/2005 | Moctezuma de la Barrera et al. | |
| 2005/0020911 A1 | 1/2005 | Viswanathan et al. | |
| 2005/0021037 A1 | 1/2005 | McCombs et al. | |
| 2005/0021039 A1 | 1/2005 | Cusick et al. | |
| 2005/0021043 A1 | 1/2005 | Jansen et al. | |
| 2005/0021044 A1 | 1/2005 | Stone et al. | |

| | | |
|---|---|---|
| 2005/0033117 A1 | 2/2005 | Ozaki et al. |
| 2005/0033149 A1 | 2/2005 | Strommer et al. |
| 2005/0038337 A1 | 2/2005 | Edwards |
| 2005/0049477 A1 | 3/2005 | Fu et al. |
| 2005/0049478 A1 | 3/2005 | Kuduvalli et al. |
| 2005/0049485 A1 | 3/2005 | Harmon et al. |
| 2005/0049486 A1 | 3/2005 | Urquhart et al. |
| 2005/0054915 A1 | 3/2005 | Sukovic et al. |
| 2005/0054916 A1 | 3/2005 | Mostafavi |
| 2005/0059873 A1 | 3/2005 | Glozman et al. |
| 2005/0075632 A1 | 4/2005 | Russell et al. |
| 2005/0080334 A1 | 4/2005 | Willis |
| 2005/0085714 A1 | 4/2005 | Foley et al. |
| 2005/0085715 A1 | 4/2005 | Dukesherer et al. |
| 2005/0085717 A1 | 4/2005 | Shahidi |
| 2005/0085718 A1 | 4/2005 | Shahidi |
| 2005/0085720 A1 | 4/2005 | Jascob et al. |
| 2005/0090730 A1 | 4/2005 | Cortinovis et al. |
| 2005/0090733 A1 | 4/2005 | Van Der Lugt et al. |
| 2005/0096515 A1 | 5/2005 | Geng |
| 2005/0096535 A1 | 5/2005 | de la Barrera |
| 2005/0101970 A1 | 5/2005 | Rosenberg |
| 2005/0113659 A1 | 5/2005 | Pothier et al. |
| 2005/0113960 A1 | 5/2005 | Karau et al. |
| 2005/0119561 A1 | 6/2005 | Kienzle, III |
| 2005/0119565 A1 | 6/2005 | Pescatore |
| 2005/0119639 A1 | 6/2005 | McCombs et al. |
| 2005/0119783 A1 | 6/2005 | Brisson et al. |
| 2005/0124988 A1 | 6/2005 | Terrill-Grisoni et al. |
| 2005/0137599 A1 | 6/2005 | Masini |
| 2005/0148850 A1 | 7/2005 | Lahm et al. |
| 2005/0148855 A1 | 7/2005 | Kienzle, III |
| 2005/0197568 A1 | 9/2005 | Vass et al. |
| 2005/0197569 A1 | 9/2005 | McCombs |
| 2005/0203373 A1 | 9/2005 | Boese et al. |
| 2005/0203374 A1 | 9/2005 | Vilsmeier |
| 2005/0203375 A1 | 9/2005 | Willis et al. |
| 2005/0203383 A1 | 9/2005 | Moctezuma de la Barrera et al. |
| 2005/0203384 A1 | 9/2005 | Sati et al. |
| 2005/0215879 A1 | 9/2005 | Chuanggui |
| 2005/0215888 A1 | 9/2005 | Grimm et al. |
| 2005/0216032 A1 | 9/2005 | Hayden |
| 2005/0228250 A1 | 10/2005 | Bitter et al. |
| 2005/0228266 A1 | 10/2005 | McCombs |
| 2005/0228270 A1 | 10/2005 | Lloyd et al. |
| 2005/0228404 A1 | 10/2005 | Vandevelde |
| 2005/0234335 A1 | 10/2005 | Simon et al. |
| 2005/0234465 A1 | 10/2005 | McCombs et al. |
| 2005/0251026 A1 | 11/2005 | Stone |
| 2005/0251030 A1 | 11/2005 | Azar et al. |
| 2005/0267353 A1 | 12/2005 | Marquart et al. |
| 2005/0267354 A1 | 12/2005 | Marquart et al. |
| 2005/0267358 A1 | 12/2005 | Tuma et al. |
| 2005/0267360 A1 | 12/2005 | Birkenbach et al. |
| 2005/0267365 A1 | 12/2005 | Sokulin et al. |
| 2005/0267722 A1 | 12/2005 | Marquart et al. |
| 2005/0277832 A1 | 12/2005 | Foley et al. |
| 2005/0279368 A1 | 12/2005 | McCombs |
| 2005/0281465 A1 | 12/2005 | Marquart et al. |
| 2005/0288575 A1 | 12/2005 | de la Barrera et al. |
| 2005/0288578 A1 | 12/2005 | Durlak |
| 2006/0004284 A1 | 1/2006 | Grunschlager et al. |
| 2006/0009780 A1 | 1/2006 | Foley et al. |
| 2006/0015018 A1 | 1/2006 | Jutras et al. |
| 2006/0015030 A1 | 1/2006 | Poulin et al. |
| 2006/0025677 A1 | 2/2006 | Verard et al. |
| 2006/0025679 A1 | 2/2006 | Viswanathan et al. |
| 2006/0025681 A1 | 2/2006 | Abovitz et al. |
| 2006/0036149 A1 | 2/2006 | Lavigna et al. |
| 2006/0036151 A1 | 2/2006 | Ferre et al. |
| 2006/0036162 A1 | 2/2006 | Shahidi et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0052691 A1 | 3/2006 | Hall et al. |
| 2006/0058604 A1 | 3/2006 | Avinash et al. |
| 2006/0058615 A1 | 3/2006 | Mahajan et al. |
| 2006/0058616 A1 | 3/2006 | Marquart et al. |
| 2006/0058644 A1 | 3/2006 | Hoppe et al. |
| 2006/0058646 A1 | 3/2006 | Viswanathan |
| 2006/0058663 A1 | 3/2006 | Willis et al. |
| 2006/0161059 A1 | 7/2006 | Wilson |

FOREIGN PATENT DOCUMENTS

| | | |
|---|---|---|
| EP | 0 649 117 A2 | 4/1995 |
| EP | 0 832 609 A2 | 4/1998 |
| EP | 0 904 735 A2 | 3/1999 |
| EP | 1 226 788 A1 | 7/2002 |
| GB | 2 246 936 | 2/1992 |
| WO | WO 94/17733 A1 | 8/1994 |
| WO | WO 95/15714 A1 | 6/1995 |
| WO | WO 02/35454 A1 | 5/2002 |
| WO | WO 02/062248 A1 | 8/2002 |
| WO | WO 02/067783 A2 | 9/2002 |
| WO | WO 04/001569 A2 | 12/2003 |
| WO | WO 2004/006770 A2 | 1/2004 |
| WO | WO 2004/069036 A2 | 8/2004 |
| WO | WO 2004/069040 A2 | 8/2004 |

OTHER PUBLICATIONS

DiGioia AM, Jaramaz B; Colgan BD. Computer assisted orthopaedic surgery. Image guided and robotic assistive technologies. Clin Orthop Sep. 1998;(354):8-16.

David Stulberg S. How accurate is current TKR instrumentation? Clin Orthop. Nov. 2003;(416):177-84.

Bathis H, Perlick L, Tingart M, Luring C, Zurakowski D, Grifka J. Alignment in total knee arthroplasty. A comparison of computer-assisted surgery with the conventional technique. J Bone Joint Surg Br. 2004;86(5):682-687.

Chauhan SK, Clark GW, Lloyd S, Scott RG, Breidhal W, Sikorski JM. Computer-assisted total knee replacement: a controlled cadaver study using a multi-parameter quantitative CT assessment of alignment (the Perth CT Protocol). J Bone Joint Surg [Br] 2004;86-B:818-23.

James B. Stiehl et al., Navigation and Robotics in Total Joint and Spine Surgery, Chapter 3 C-Arm-Based Navigation, Springer-Verlag (2004) (9 pages).

"Acumen™ Surgical Navigation System, Surgical Navigation Applications" (2003) (2 pages).

Acumen™ Surgical Navigation System, Understanding Surgical Navigation (2003) (2 pages).

James B. Stiehl et al., Navigation and Robotics in Total Joint and Spine Surgery, Chapter 1 Basics of Computer-Assisted Orthopedic Surgery (CAOS), Springer-Verlag (2004) (9 pages).

Donald G. Eckhoff, Joel M. Bach, Victor M. Spitzer, Karl D. Reinig, Michelle M. Bagur, Todd H. Baldini, David Rubinstein, and Stephen Humphries, "Three-Dimensional Morphology and Kinematics of the Distal Part of the Femur Viewed in Virtual Reality. Part II," J Bone Joint Surg. Am 2003 85(Supp 4): 97-104.

"Real-Time Image Segmentation for Image-Guided Surgery" by Warfield, Simon; 14 pages; http://splweb.bwh.harvard.edu:8000/pages/papers/warfield/sc98/; accepted to appear at SC98.

"A Computer-Assisted Total Knee Replacement Surgical System Using a Calibrated Robot," Thomas C. Kienzle III, S. David Stulburg, Michael Peshkin, Arthur Quaid, Jon Lea, Ambarish Goswami, and Chi-Haur Wu, in "Computer-Integrated Surgery: Technology and Clinical Applications," ed. Russell H. Taylor, et. al., 1996 MIT Press. (28 pages).

Luck, J.P., Debrunner, C., Hoff, W., He, Q., and Small, D. "Development and Analysis of a Real-Time Human Motion Tracking System," in *Proc. of Workshop on Applications of Computer Vision*. 2002. Orlando, FL, IEEE (7 pages).

DiFranco. D.E. et al., "Recovery of 3D Articulated Motion from 2D Correspondences," Cambridge Research Laboratory Technical Report CRL 99/7, Dec. 1999 (20 pages).

Traxtal Technologies—Virtual Keypad, (printed May 23, 2005) pp. 1-2, http://www.traxtal.com/products/products_input_virtualkeypad.htm?print.

C. Graetzel, T.W. Fong, S. Grange, and C. Baur, "A non-contact mouse for surgeon-computer interaction," Technology and Health Care, vol. 12, No. 3, 2004, pp. 245-257.

Habets, R.J.E.: *Computer assistance in orthopaedic surgery*. Promoters: prof.dr.ir. A. Hasman, prof.dr.ir. F.A. Gerritsen; copromoter: dr.ir. J.A. Blom. Technische Universiteit Eindhoven, ISBN 90-386-1940-5, Nov. 4, 2002. (4 pages).

Visarius H, Gong J, Scheer C, Haralamb S, Nolte LP, Man-machine interfaces in computer assisted surgery. Comput Aid Surg 1997;2:102-107.

Crosby, N. Scott, et al., Computer-aided radiation therapy simulation: image intensifier spatial distortion correction for large field of view digital fluoroscopy, IOP Electronic Journals, Phys. Med. Biol., vol. 43, 1998, pp. 2265-2278.

* cited by examiner

IMAGE GUIDED TRACKING ARRAY AND METHOD

This application claims the benefit of U.S. Provisional Patent Application Ser. No. 60/694,178, filed Jun. 27, 2005.

FIELD OF THE INVENTION

The present teachings relate to surgical navigation and more particularly to tracking arrays and methods for using tracking arrays with a surgical navigation system.

BACKGROUND

Surgical navigation systems, also known as computer assisted surgery and image guided surgery, aid surgeons in locating patient anatomical structures, guiding surgical instruments, and implanting medical devices with a high degree of accuracy. Surgical navigation has been compared to a global positioning system that aids vehicle operators to navigate the earth. A surgical navigation system typically includes a computer, a tracking system, and patient anatomical information. The patient anatomical information can be obtained by using an imaging mode such a fluoroscopy, computer tomography (CT) or by simply defining the location of patient anatomy with the surgical navigation system. Surgical navigation systems can be used for a wide variety of surgeries to improve patient outcomes.

To successfully implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct pre-operative and intra-operative body imaging.

To accomplish the accurate planning, tracking and navigation of surgical instruments, tools and/or medical devices during an image guided surgery procedure, surgeons often utilize "tracking arrays" that are coupled to the surgical components. The tracking arrays allow the surgeon to accurately track the location of these surgical components, as well as the patient's bones during the surgery. By knowing the physical location of the tracking array, the software detection program of the tracking system is able to calculate the position of the tracked component relative to a surgical plan image.

Because of the complexity of many image guided surgery procedures, surgeons often need to use many different tracking arrays during a single procedure. As such, several different tracking arrays must be purchased, prepared and configured for the operating room environment. It would be desirable to overcome these and other shortcomings of the prior art.

SUMMARY OF THE INVENTION

The present teachings provide an adjustable tracking array and method of using it with an image guided surgery navigation system that reduces the number of arrays required during a surgical procedure.

In one exemplary embodiment, the present teachings provide an array for use with a surgical navigation system. The array comprises a frame and first, second and third markers attached to the frame, the first, second and third markers being detectable by a tracking system used in a surgical navigation system. The first marker is movable relative to the frame.

In another exemplary embodiment, a method of performing a surgery using surgical navigation is provided. The method uses a tracking system and an array having a frame with first, second and third markers attached thereto, the array being identified and tracked by the tracking system. A first surgical component to which the array is attached is used during the surgery while the first surgical component is tracked by the tracking system. The array is detached from the first surgical component and reattached to a second surgical component. The position of the first marker is moved from a first position to a second position relative to the frame, and the tracking system identifies the second surgical component to which the array is attached. The second surgical component to which the array is attached is then used during the surgery and tracked by the tracking system.

BRIEF DESCRIPTION OF DRAWINGS

The above-mentioned aspects of the present teachings and the manner of obtaining them will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present teachings described below are not intended to be exhaustive or to limit the invention to the precise forms disclosed in the following detailed description. Rather, the embodiments are chosen and described so that others skilled in the art may appreciate and understand the principles and practices of the present teachings.

Figure 1:
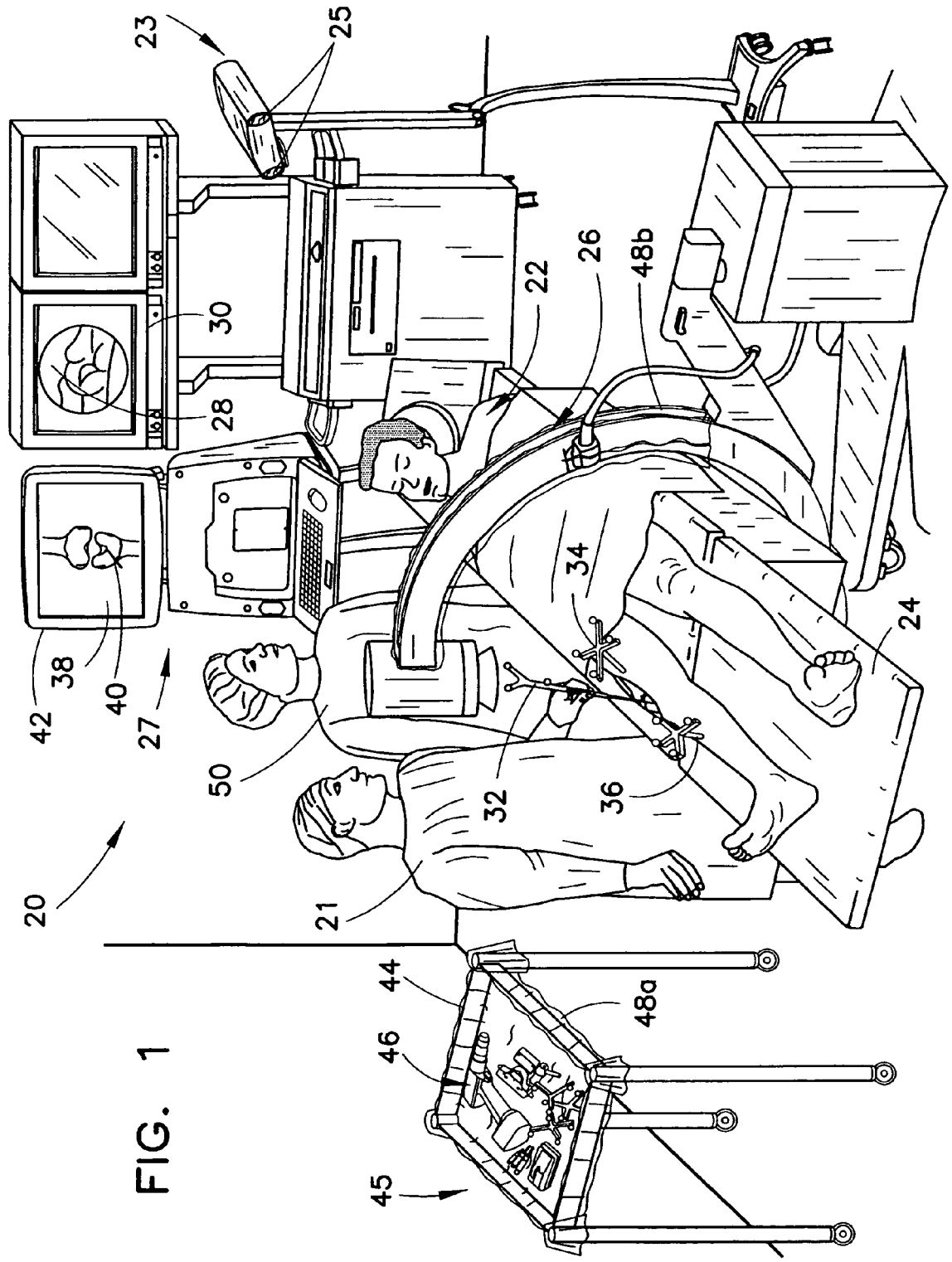
FIG. 1 is a perspective view of an exemplary operating room setup in a surgical navigation embodiment in accordance with the present teachings.

FIG. 1 shows a perspective view of an operating room with surgical navigation system 20. Surgeon 21 is aided by the surgical navigation system in performing knee arthroplasty, also known as knee replacement surgery, on patient 22 shown lying on operating table 24. Surgical navigation system 20 has a tracking system that locates arrays and tracks them in real-time. To accomplish this, the surgical navigation system includes optical locator 23, which has two CCD (charge couple device) cameras 25 that detect the positions of the arrays in space by using triangulation methods. The relative location of the tracked arrays, including the patient's anatomy, can then be shown on a computer display (such as computer display 27 for instance) to assist the surgeon during the surgical procedure. The arrays that are typically used include probe arrays, instrument arrays, reference arrays, and calibrator arrays. The operating room includes an imaging system such as C-arm fluoroscope 26 with fluoroscope display image 28 to show a real-time image of the patient's knee on monitor 30. Surgeon 21 uses surgical probe 32 to reference a point on the patient's knee, and reference arrays 34, 36 attached to the patient's femur and tibia to provide known anatomic reference points so the surgical navigation system can compensate for leg movement. The relative location of probe array 32 to the patient's tibia is then shown as reference numeral 40 on computer display image 38 of computer monitor 42. The operating room also includes instrument cart 45 having tray 44 for holding a variety of surgical instruments and arrays 46. Instrument cart 45 and C-arm 26 are typically draped in sterile covers 48a, 48b to eliminate contamination risks within the sterile field.

The surgery is performed within a sterile field, adhering to the principles of asepsis by all scrubbed persons in the operating room. Patient 22, surgeon 21 and assisting clinician 50 are prepared for the sterile field through appropriate scrubbing and clothing. The sterile field will typically extend from operating table 24 upward in the operating room. Typically both computer display image 38 and fluoroscope display image 28 are located outside of the sterile field.

A representation of the patient's anatomy can be acquired with an imaging system, a virtual image, a morphed image, or a combination of imaging techniques. The imaging system can be any system capable of producing images that represent the patient's anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with surgical navigation system 20 or by applying a statistical anatomical model. A morphed image of the patient's anatomy can be created by combining an image of the patient's anatomy with a data set, such as a virtual image of the patient's anatomy. Some imaging systems, such as C-arm fluoroscope 26, can require calibration. The C-arm can be calibrated with a calibration grid that enables determination of fluoroscope projection parameters for different orientations of the C-arm to reduce distortion. A registration phantom can also be used with a C-arm to coordinate images with the surgical navigation application program and improve scaling through the registration of the C-arm with the surgical navigation system. A more detailed description of a C-arm based navigation system is provided in James B. Stiehl et al., Navigation and Robotics in Total Joint and Spine Surgery, Chapter 3 C-Arm-Based Navigation, Springer-Verlag (2004).

Figure 2:
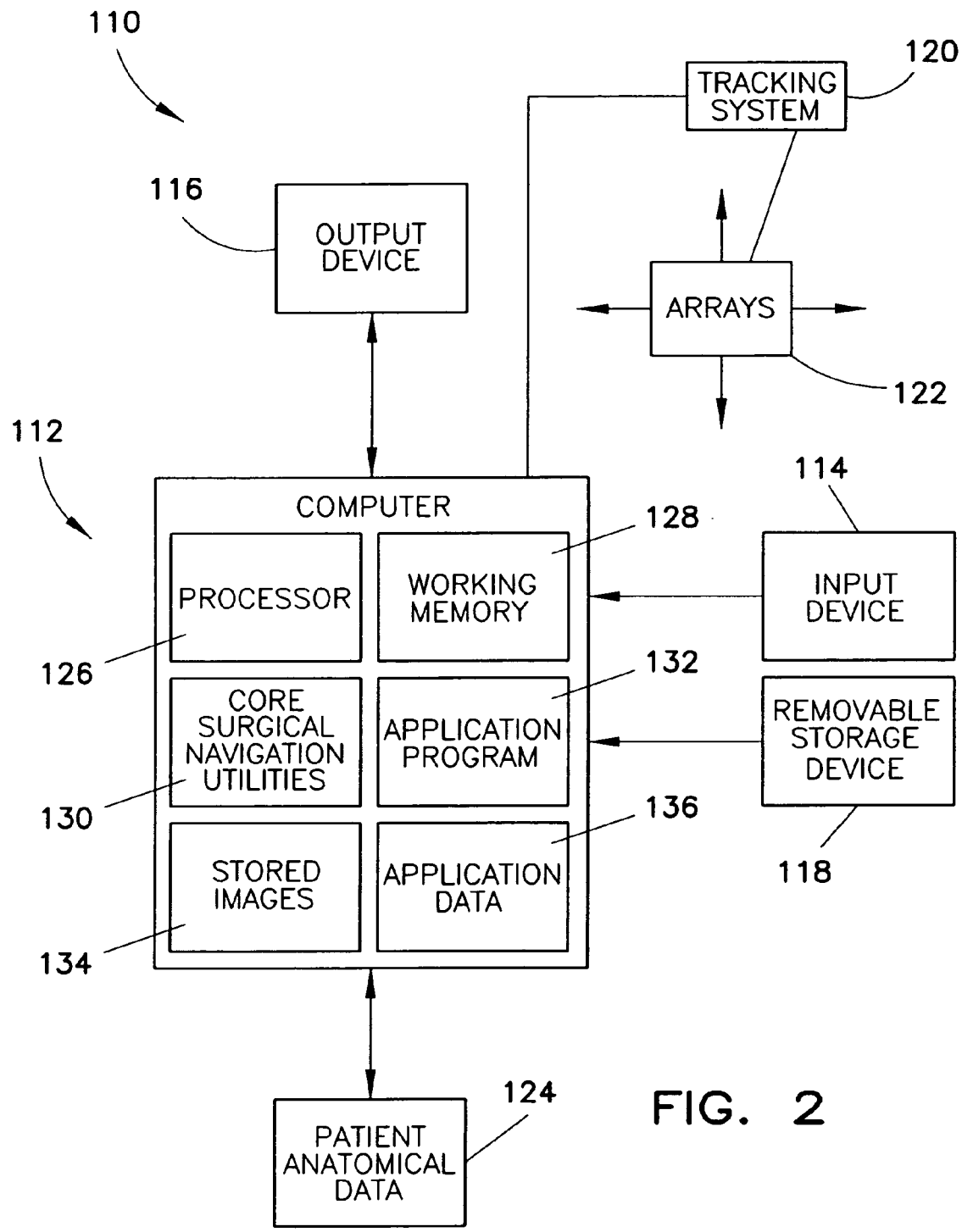
FIG. 2 is an exemplary block diagram of a surgical navigation system embodiment in accordance with the present teachings.

FIG. 2 is a block diagram of an exemplary surgical navigation system embodiment in accordance with the present teachings, such as an Acumen™ Surgical Navigation System available from EBI, L.P., Parsipanny, N.J. USA, a Biomet Company. The surgical navigation system 110 comprises computer 112, input device 114, output device 116, removable storage device 118, tracking system 120, arrays 122, and patient anatomical data 124, as further described in the brochure Acumen™ Surgical Navigation System, Understanding Surgical Navigation (2003), available from EBI, L.P. The Acumen™ Surgical Navigation System can operate in a variety of imaging modes such as a fluoroscopy mode creating a two-dimensional x-ray image, a computer-tomography (CT) mode creating a three-dimensional image, and an imageless mode creating a virtual image or planes and axes by defining anatomical points of the patient's anatomy. In the imageless mode, a separate imaging device such as a C-arm is not required, thereby simplifying set-up. The Acumen™ Surgical Navigation System can run a variety of orthopedic applications, including applications for knee arthroplasty, hip arthroplasty, spine surgery, and trauma surgery, as further described in the brochure "Acumen™ Surgical Navigation System, Surgical Navigation Applications" (2003) available from EBI, L.P. A more detailed description of an exemplary surgical navigation system is provided in James B. Stiehl et al., Navigation and Robotics in Total Joint and Spine Surgery, Chapter 1 Basics of Computer-Assisted Orthopedic Surgery (CAOS), Springer-Verlag (2004).

Computer 112 can be any computer capable of properly operating surgical navigation devices and software, such as a computer similar to a commercially available personal computer that comprises a processor 126, working memory 128, core surgical navigation utilities 130, an application program 132, stored images 134, and application data 136. Processor 126 is a processor of sufficient power for computer 112 to perform desired functions, such as one or more microprocessors. Working memory 128 is memory sufficient for computer 112 to perform desired functions such as solid-state memory, random-access memory, and the like. Core surgical navigation utilities 130 are the basic operating programs, and include image registration, image acquisition, location algorithms, orientation algorithms, virtual keypad, diagnostics, and the like. Application program 132 can be any program configured for a specific surgical navigation purpose, such as orthopedic application programs for unicondylar knee ("uni-kee"), total knee, hip, spine, trauma, intramedullary ("IM") nail, and external fixator. Stored images 134 are those recorded during image acquisition using any of the imaging systems previously discussed. Application data 136 is data that is generated or used by application program 132, such as implant geometries, instrument geometries, surgical defaults, patient landmarks, and the like. Application data 136 can be pre-loaded in the software or input by the user during a surgical navigation procedure.

Output device 116 can be any device capable of creating an output useful for surgery, such as a visual output and an auditory output. The visual output device can be any device capable of creating a visual output useful for surgery, such as a two-dimensional image, a three-dimensional image, a holographic image, and the like. The visual output device can be a monitor for producing two and three-dimensional images, a projector for producing two and three-dimensional images, and indicator lights. The auditory output can be any device capable of creating an auditory output used for surgery, such as a speaker that can be used to provide a voice or tone output.

Removable storage device 118 can be any device having a removable storage media that would allow downloading data such as application data 136 and patient anatomical data 124. The removable storage device can be a read-write compact disc (CD) drive, a read-write digital video disc (DVD) drive, a flash solid-state memory port, a removable hard drive, a floppy disc drive, and the like.

Tracking system 120 can be any system that can determine the three-dimensional location of devices carrying or incorporating markers that serve as tracking indicia. An active tracking system has a collection of infrared light emitting diode (ILEDs) illuminators that surround the position sensor lenses to flood a measurement field of view with infrared light. A passive system incorporates retro-reflective markers that reflect infrared light back to the position sensor, and the system triangulates the real-time position (x, y, and z location) and orientation (rotation around x, y, and z axes) of an array 122 and reports the result to the computer system with an accuracy of about 0.35 mm Root Mean Squared (RMS). An example of passive tracking system is a Polaris® Passive System and an example of a marker is the NDI Passive Spheres™ both available from Northern Digital Inc. Ontario, Canada. A hybrid tracking system can detect active and active wireless markers in addition to passive markers. Active marker based instruments enable automatic tool identification, program control of visible LEDs, and input via tool buttons. An example of a hybrid tracking system is the Polaris® Hybrid System available from Northern Digital Inc. A marker can be a passive IR reflector, an active IR emitter, an electromagnetic marker, and an optical marker used with an optical camera.

Arrays 122 can be probe arrays, instrument arrays, reference arrays, calibrator arrays, and the like. Arrays 122 can have any number of markers, but typically have three or more markers to define real-time position (x, y, and z location) and orientation (rotation around x, y, and z axes). As will be explained in greater detail below, an array comprises a body and markers. The body comprises an area for spatial separation of markers. In some embodiments, there are at least two arms and some embodiments can have three arms, four arms, or more. The arms are typically arranged asymmetrically to facilitate specific array and marker identification by the tracking system. In other embodiments, such as a calibrator array, the body provides sufficient area for spatial separation of markers without the need for arms. Arrays can be disposable or non-disposable. Disposable arrays are typically manufactured from plastic and include installed markers. Non-disposable arrays are manufactured from a material that can be sterilized, such as aluminum, stainless steel, and the like. The markers are removable, so they can be removed before sterilization.

Planning and collecting patient anatomical data 124 is a process by which a clinician inputs into the surgical navigation system actual or approximate anatomical data. Anatomical data can be obtained through techniques such as anatomic painting, bone morphing, CT data input, and other inputs, such as ultrasound and fluoroscope and other imaging systems.

Figure 3:
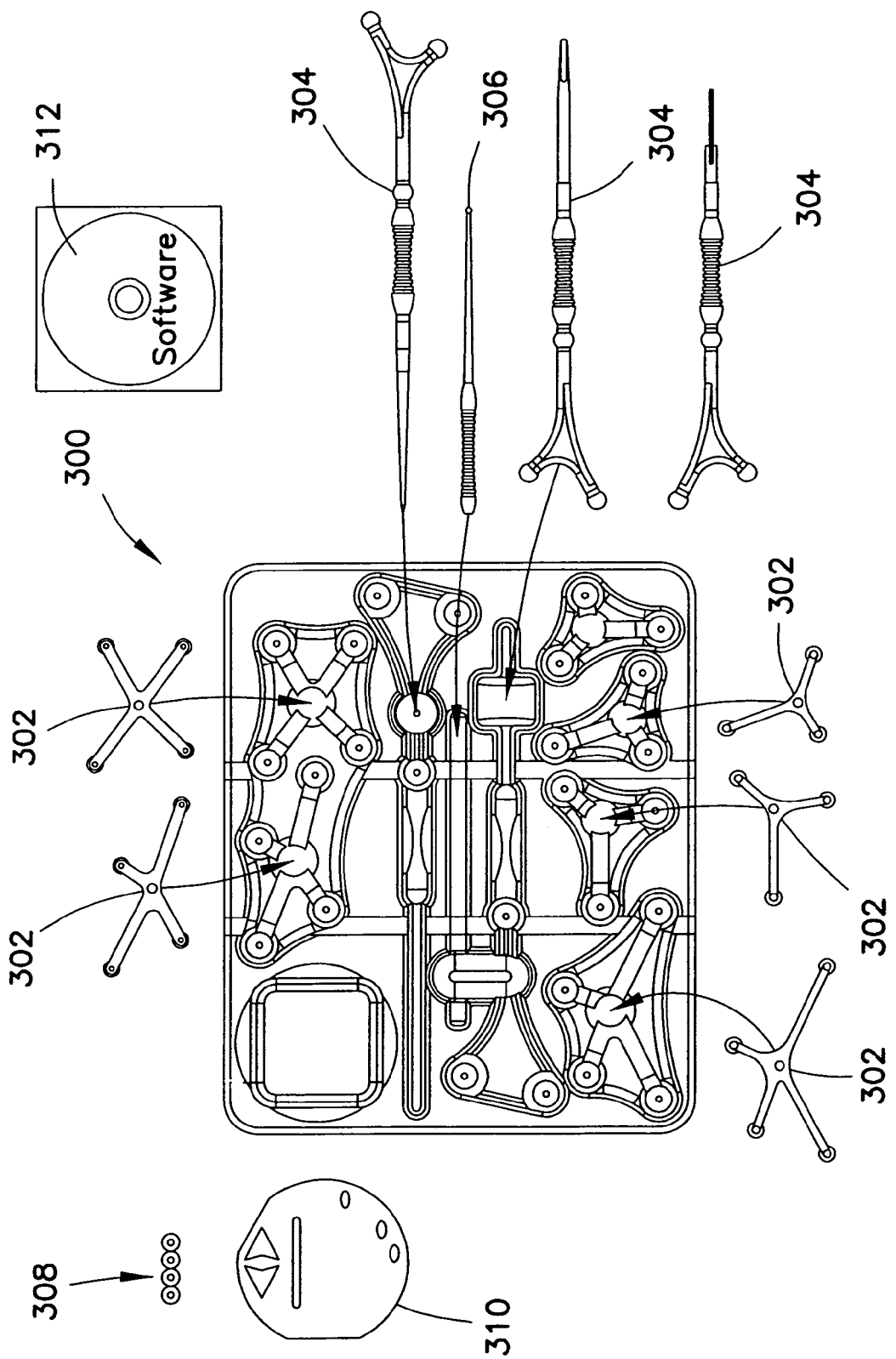
FIG. 3 is an exemplary surgical navigation kit embodiment in accordance with the present teachings.

FIG. 3 shows orthopedic application kit 300, which is used in accordance with the present teachings. Application kit 300 is typically carried in a sterile bubble pack and is configured for a specific surgery. Exemplary kit 300 comprises arrays 302, surgical probes 304, stylus 306, markers 308, virtual keypad template 310, and application program 312. Orthopedic application kits are available for unicondylar knee, total knee, total hip, spine, and external fixation from EBI, L.P.

Figure 4:
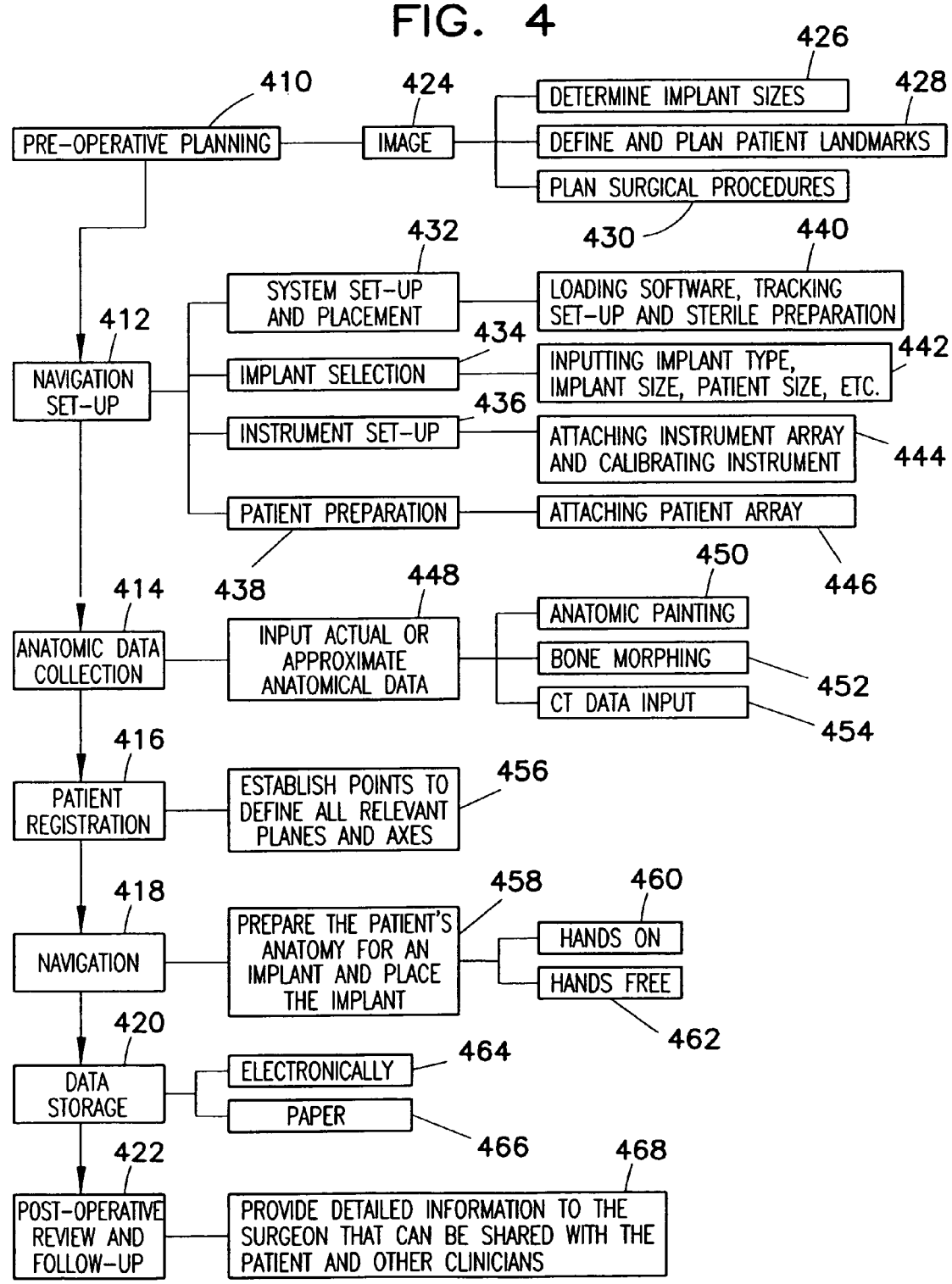
FIG. 4 is a flowchart illustrating the operation of an exemplary surgical navigation system in accordance with the present teachings.

FIG. 4 shows an exemplary illustration of surgical navigation system 20. The process of surgical navigation according to this exemplary embodiment includes pre-operative planning 410, navigation set-up 412, anatomic data collection 414, patient registration 416, navigation 418, data storage 420, and post-operative review and follow-up 422.

Pre-operative planning 410 is performed by generating an image 424, such as a CT scan that is imported into the computer. With image 424 of the patient's anatomy, the surgeon can then determine implant sizes 426, such as screw lengths, define and plan patient landmarks 428, such as long leg mechanical axis, and plan surgical procedures 430, such as bone resections and the like. Pre-operative planning 410 can reduce the length of intra-operative planning thus reducing overall operating room time.

Navigation set-up 412 includes the tasks of system set-up and placement 432, implant selection 434, instrument set-up 436, and patient preparation 438. System set-up and placement 432 includes loading software, tracking set-up, and sterile preparation 440. Software can be loaded from a pre-installed application residing in memory, a single use software disk, or from a remote location using connectivity such as the internet. A single use software disk contains an application that will be used for a specific patient and procedure that can be configured to time-out and become inoperative after a period of time to reduce the risk that the single use software will be used for someone other than the intended patient. The single use software disk can store information that is specific to a patient and procedure that can be reviewed at a later time. Tracking set-up involves connecting all cords and placement of the computer, camera, and imaging device in the operating room. Sterile preparation involves placing sterile plastic on selected parts of the surgical navigation system and imaging equipment just before the equipment is moved into a sterile environment, so the equipment can be used in the sterile field without contaminating the sterile field.

Navigation set-up 412 is completed with implant selection 434, instrument set-up 436, and patient preparation 438. Implant selection 434 involves inputting into the system information such as implant type, implant size, patient size, and the like 442. Instrument set-up 436 involves attaching an instrument array to each instrument intended to be used and then calibrating each instrument 444. Instrument arrays should be placed on instruments, so the instrument array can be acquired by the tracking system during the procedure. Patient preparation 438 is similar to instrument set-up because an array is typically rigidly attached to the patient's anatomy 446. Reference arrays do not require calibration but should be positioned so the reference array can be acquired by the tracking system during the procedure.

As mentioned above, anatomic data collection 414 involves a clinician inputting into the surgical navigation system actual or approximate anatomical data 448. Anatomical data can be obtained through techniques such as anatomic painting 450, bone morphing 452, CT data input 454, and other inputs, such as ultrasound and fluoroscope and other imaging systems. The navigation system can construct a bone model with the input data. The model can be a three-dimensional model or two-dimensional pictures that are coordinated in a three-dimensional space. Anatomical painting 450 allows a surgeon to collect multiple points in different areas of the exposed anatomy. The navigation system can use the set of points to construct an approximate three-dimensional model of the bone. The navigation system can use a CT scan done pre-operatively to construct an actual model of the bone. Fluoroscopy uses two-dimensional images of the actual bone that are coordinated in a three-dimensional space. The coordination allows the navigation system to accurately display the location of an instrument that is being tracked in two separate views. Image coordination is accomplished through a registration phantom that is placed on the image intensifier of the C-arm during the acquisition of images. The registration phantom is a tracked device that contains imbedded radio-opaque spheres. The spheres have varying diameters and reside on two separate planes. When an image is taken, the fluoroscope transfers the image to the navigation system. Included in each image are the imbedded spheres. Based on previous calibration, the navigation system is able to coordinate related anterior and posterior views and coordinate related medial and lateral views. The navigation system can also compensate for scaling differences in the images.

Patient registration 416 establishes points that are used by the navigation system to define all relevant planes and axes 456. Patient registration 416 can be performed by using a probe array to acquire points, placing a software marker on a stored image, or automatically by software identifying anatomical structures on an image or cloud of points. Once registration is complete, the surgeon can identify the position of tracked instruments relative to tracked bones during the surgery. The navigation system enables a surgeon to interactively reposition tracked-instruments to match planned positions and trajectories and assists the surgeon in navigating the patient's anatomy.

During the procedure, step-by-step instructions for performing the surgery in the application program are provided by a navigation process. Navigation 418 is the process a surgeon uses in conjunction with a tracked instrument or other tracked array to precisely prepare the patient's anatomy for an implant and to place the implant 458. Navigation 418 can be performed hands-on 460 or hands-free 462. However navigation 418 is performed, there is usually some form of feedback provided to the clinician such as audio feedback or visual feedback or a combination of feedback forms. Positive feedback can be provided in instances such as when a desired point is reached, and negative feedback can be provided in instances such as when a surgeon has moved outside a pre-determine parameter. Hands-free 462 navigation involves manipulating the software through gesture control, tool recognition, virtual keypad and the like. Hands-free 462 is done to avoid leaving the sterile field, so it may not be necessary to assign a clinician to operate the computer outside the sterile field.

Data storage 420 can be performed electronically 464 or on paper 466, so information used and developed during the process of surgical navigation can be stored. The stored information can be used for a wide variety of purposes such as monitoring patient recovery and potentially for future patient revisions. The stored data can also be used by institutions performing clinical studies.

Post-operative review and follow-up 422 is typically the final stage in a procedure. As it relates to navigation, the surgeon now has detailed information that he can share with the patient or other clinicians 468.

Embodiments incorporating the present teachings enhance the above described surgical navigation process by implementing an adjustable tracking array and method of use into surgical navigation system 20. Generally speaking, the array includes a frame and at least three markers attached to the frame, wherein the markers are detectable by a tracking system used in surgical navigation. At least one of the markers is movable or transferable relative to the frame, particularly in a co-planar direction that changes the three-dimensional configuration of the array. More particularly, at least one marker moves in a two dimensional direction relative to the frame. In other words, the marker moves with respect to the frame such that the three-dimensional configuration of the markers changes and the tracking system recognizes the change. In this manner, a single array can be reconfigured or repositioned into multiple configurations that are identifiable and distinguishable by the tracking system, thereby reducing the overall number of arrays needed during an image guided procedure.

In certain exemplary embodiments, at least one marker slides along the frame from a first position where it can be held in place to a second position where it can also be held in place. In other embodiments, one or more of the markers may be detached from the frame at a first position and then reattached to the frame at a second position. In still other embodiments, a portion of the frame itself may move together with the movable marker. Advantageously, embodiments incorporating the present teachings are economical because a single array may be used for what formerly required two, three or more separate arrays.

Referring now to FIGS. 5A-5D, exemplary tracking array 500 is shown associated with surgical component 540. Tracking array 500 includes frame 502 and markers 504, 506, 508, which are attached to the frame yet repositionable relative to the frame. That is, one or more of the markers are releasably secured or mounted to the frame in such a manner that they may be moved or displaced relative to the frame from a first position to a second position. Frame 502 is generally "T-shaped" and is defined by arm members 501a, 501b, 501c. Array coupling member 520 is disposed at one end of frame 502 and assists in releasably and interchangeably connecting or attaching the tracking array to at least two different surgical components, one of which being surgical component 540, for instance. While tracking array 500 is generally "T-shaped," other frame configurations having at least three markers attached may be used in accordance with the teachings of the present invention. Such alternate configurations include, but are not limited to, Y-shaped, F-shaped, X-shaped, V-shaped, U-shaped and L-shaped structures.

Figure 5A:
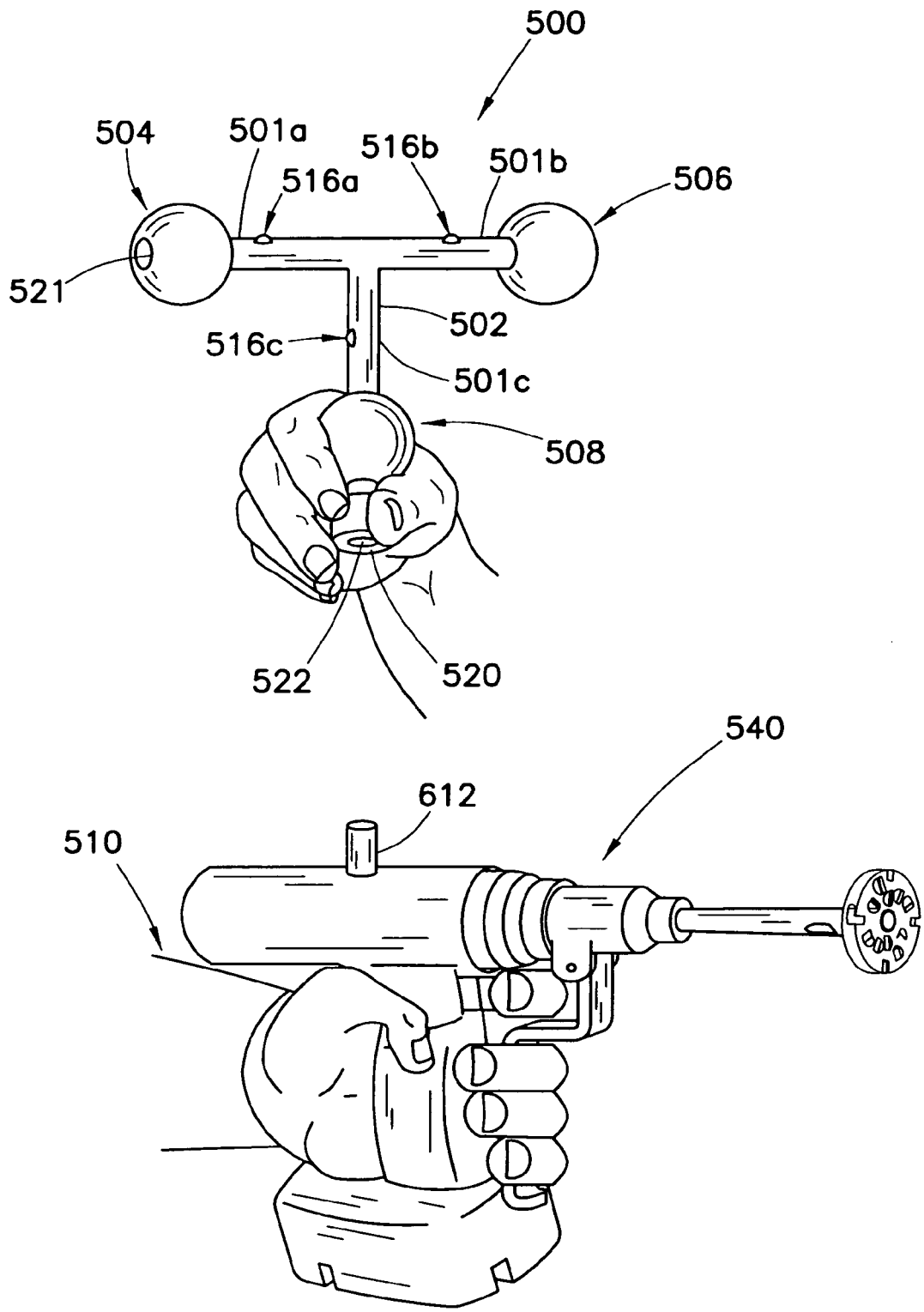
FIGS. 5A-5D are perspective views illustrating an example of an exemplary tracking array being attached to and detached from surgical components and having first and second markers moved by a physician in accordance with the present teachings.
Figure 5B:
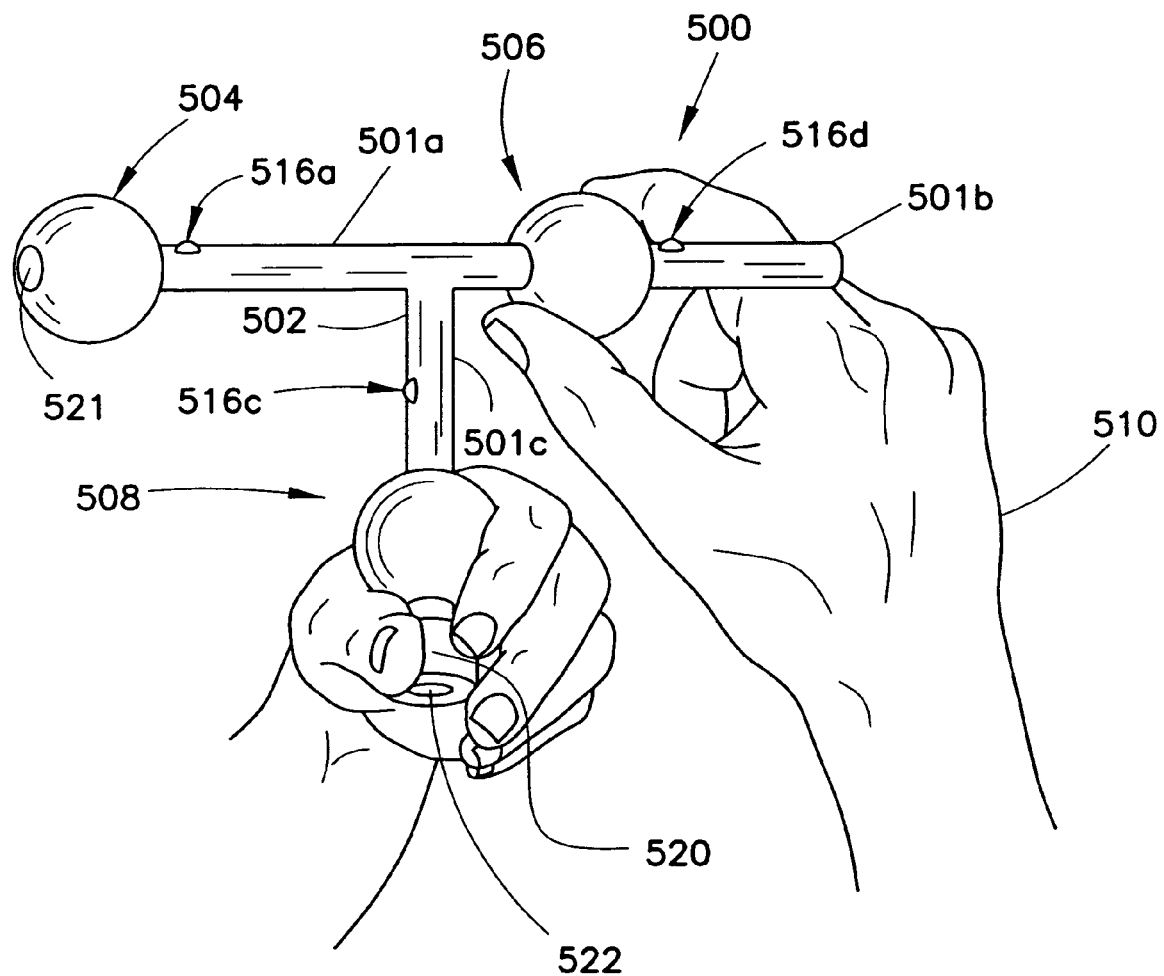
Figure 5C:
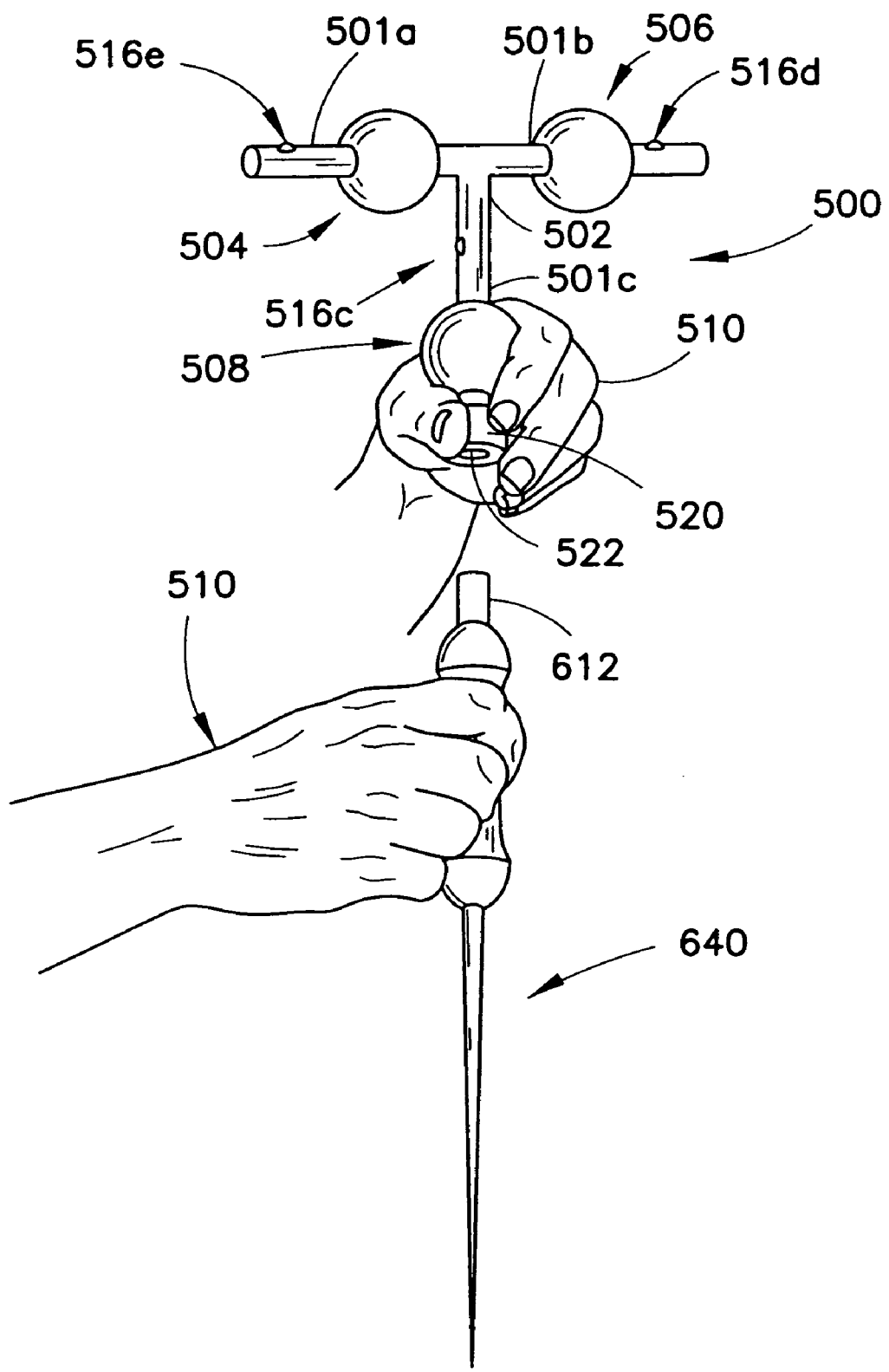
Figure 5D:
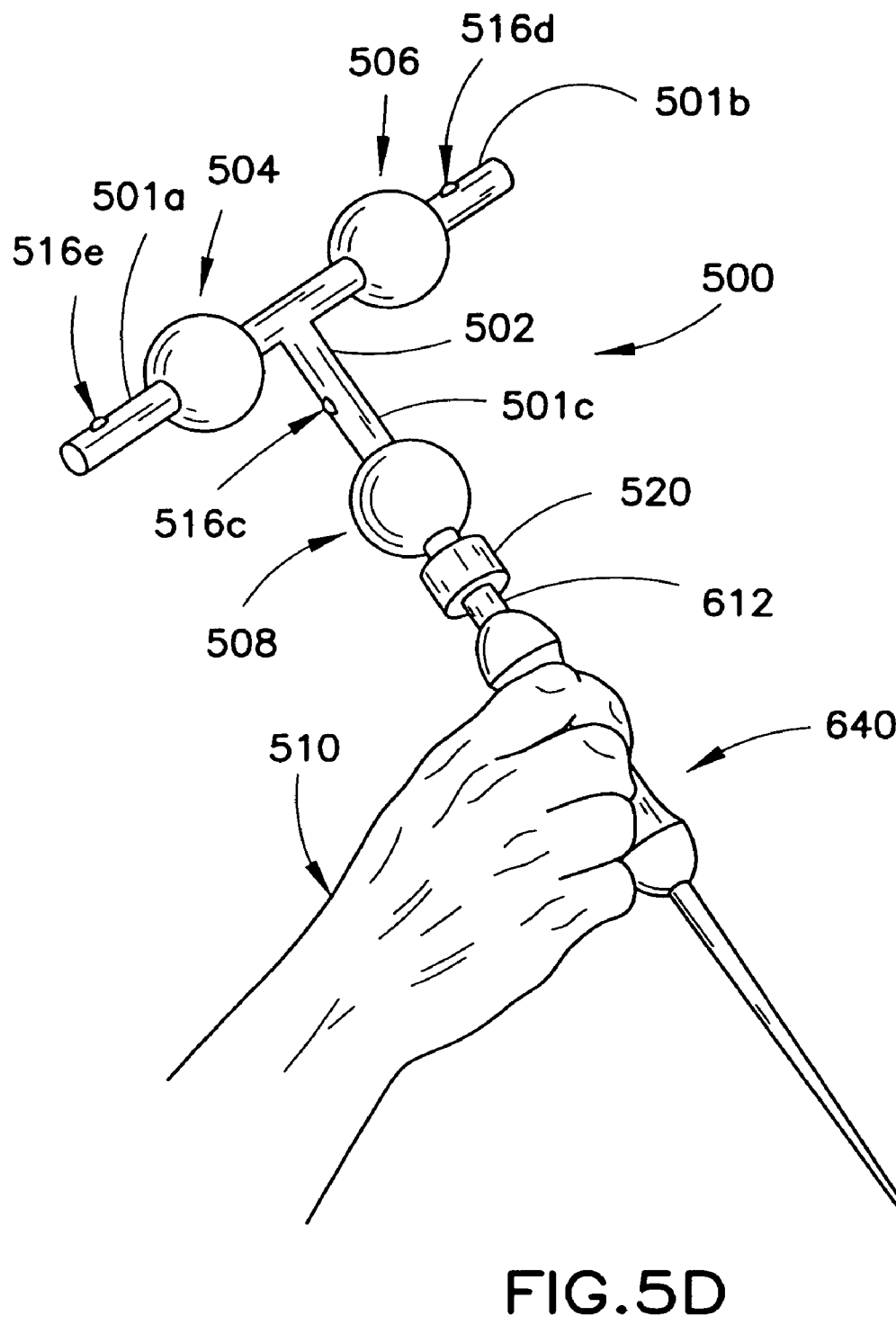

Frame 502 has a plurality of retaining means or retainers 516a, 516b, 516c positioned along arm members 501a, 501b, 501c that allow markers 504, 506, 508 to be releasably secured to the frame. More particularly, each of markers 504, 506, 508 has a bore 521 extending through its center so that physician 510 can slide one or more of the markers relative to the frame and position them at any desired retainer position or location. For example, in FIG. 5B marker 506 is held in place at the location of retainer 516b (as seen in FIG. 5A) after being moved from its position shown in FIG. 5A. By moving marker 506 to the location of retainer 516b, physician 510 exposes retainer 516d, which was initially covered by marker 506. FIGS. 5C and 5D depict markers 506 and 504 being moved to the location of retainers 516b and 516a, thereby exposing retainers 516d and 516e.

To track the position of a surgical component during an image guided surgery procedure, tracking array 500 is attached to the component by inserting the component's device-coupling member 612 into internal bore 522 of array coupling member 520. For instance, FIG. 5D illustrates exemplary tracking array 500 attached to surgical instrument 640. It should be understood that the attachment between tracking array 500 and surgical instrument 640 may be achieved by any attachment means readily known within the art. Such attachment means include, but are not limited to, threading, snap-connections, quick connections and the like.

Figure 6:
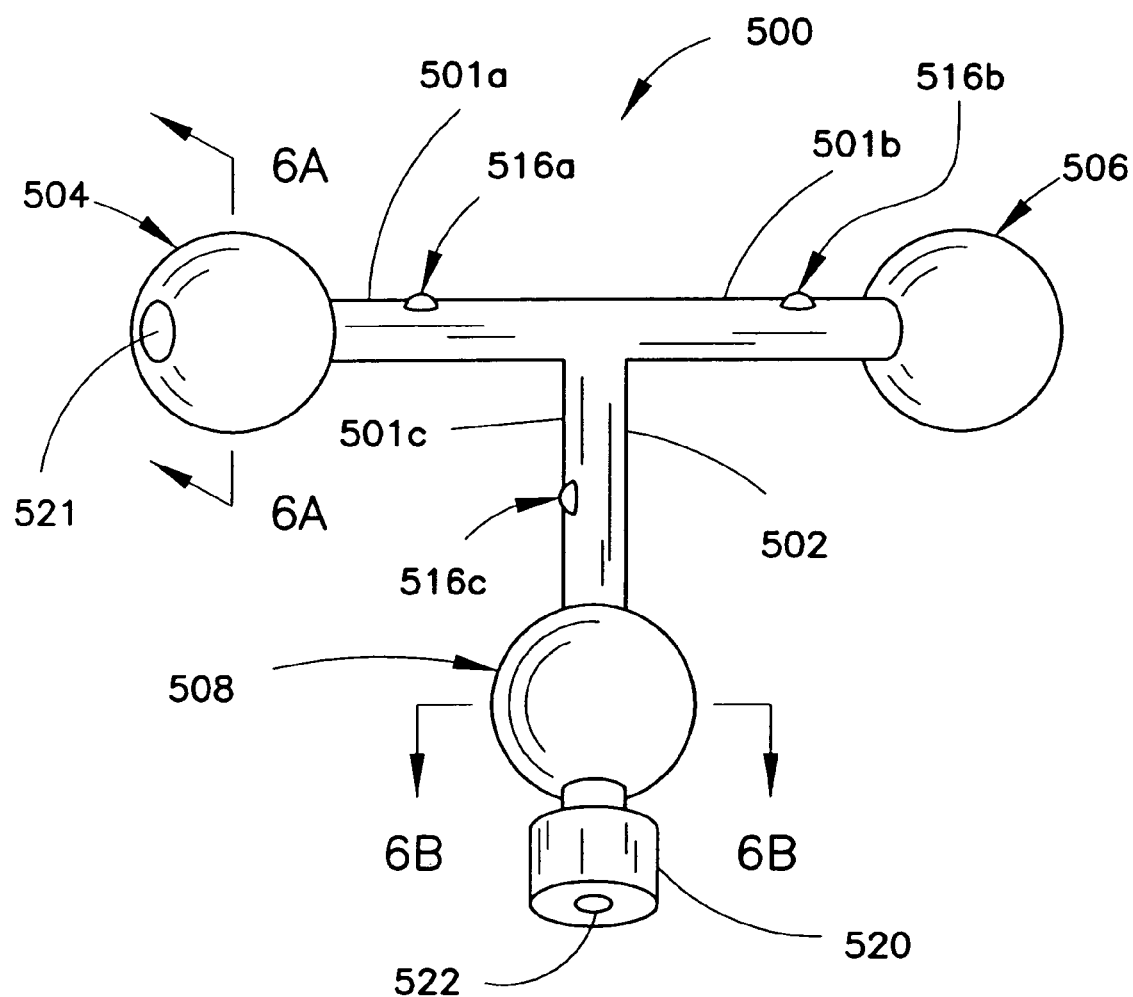
FIG. 6 is a perspective view of an exemplary tracking array in accordance with the present teachings.
Figure 6A:
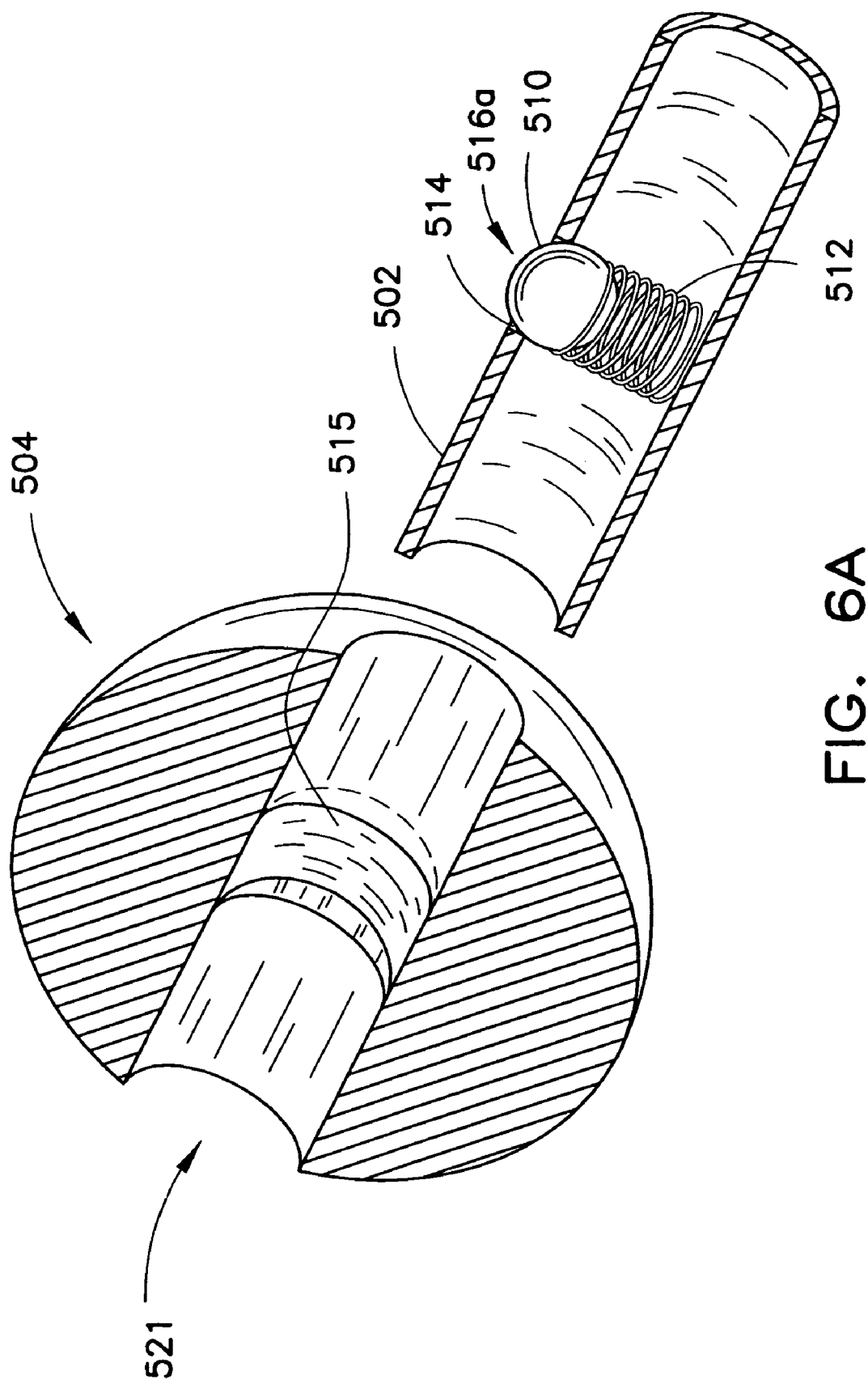
FIG. 6A is a sectional view of the exemplary tracking array of FIG. 6 taken along line 6A-6A.

Referring now to FIG. 6, an exemplary illustration of adjustable tracking array 500 is depicted. According to this exemplary illustration, markers 504, 506, 508 are positioned along frame 502 such that retainers 516a, 516b and 516c are exposed. To reposition and secure markers 504, 506, 508 to frame 502, retainers 516a, 516b, 516c, 516d, 516e, 516f each include a displaceable retainer device 510 and biasing means 512 (see FIG. 6A, which is a sectional view of marker 504 taken along line 6A-6A of FIG. 6) for urging the retainer device radially inwardly or outwardly relative to opening 514. Useful biasing means include any device capable of allowing inward and outward radial movement, such as springs, elastic components, magnets, or the like. Furthermore, each marker 504, 506, 508 has a groove 515 formed in its cylindrical bore for receiving the protruding portion of retainer device 510 (i.e., the portion physically extending outside of frame 502) and for attaching markers 504, 506, 508 at a desired retainer location (516a, 516b, 516c, 516d, 516e, 516f).

Figure 6B:
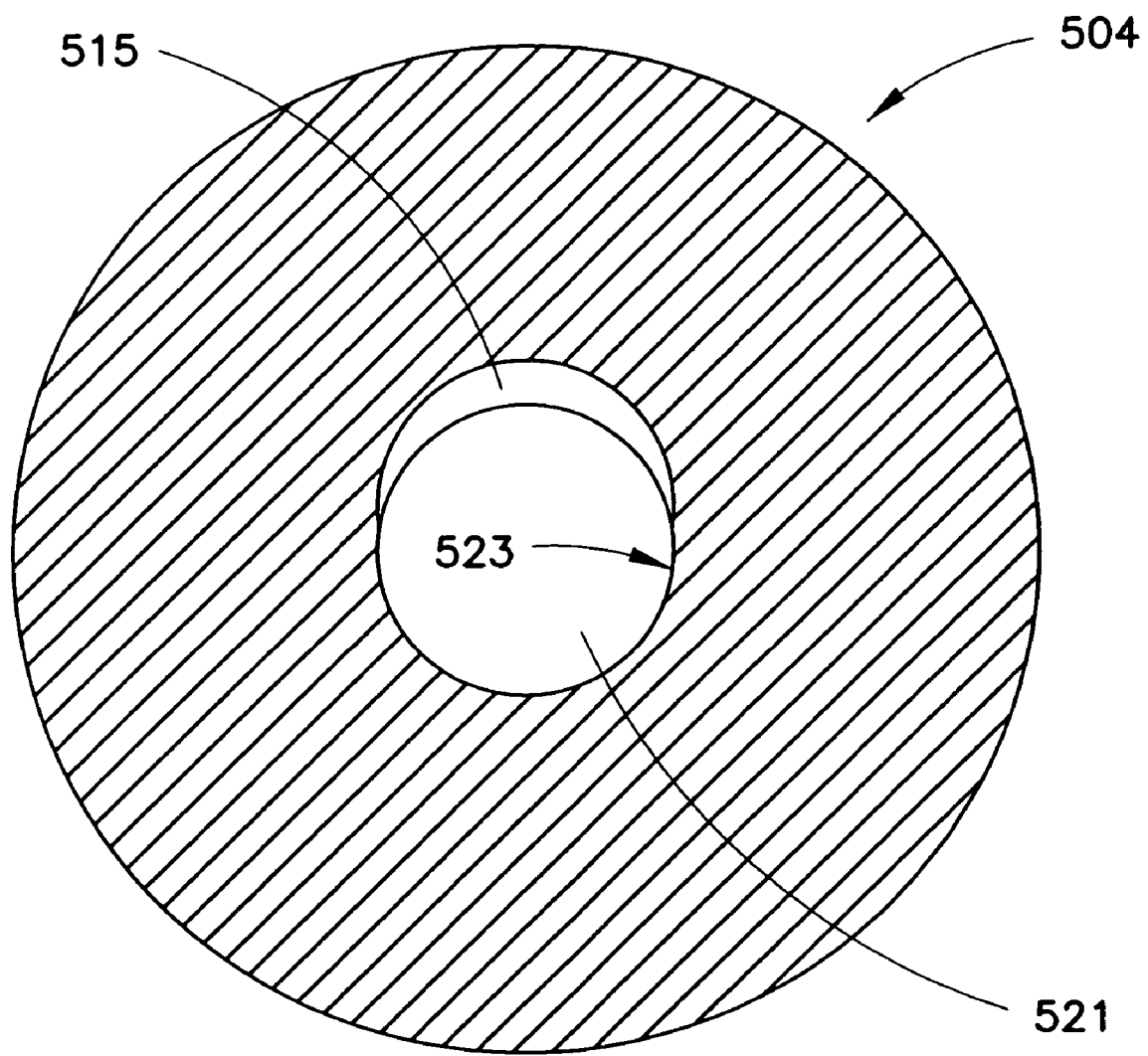
FIG. 6B is a sectional view of the exemplary tracking array of FIG. 6 taken along line 6B-6B.

According to an exemplary illustration, the outside surface of frame 502 has a shape complementary to that of central bore 521 of markers 504, 506, 508 such that the markers can slide along frame 502 from a first retainer to a second retainer. Once the marker reaches the location of the retainer (516a, 516b, 516c, 516d, 516e, 516f) to which the physician desires the marker to remain, retainer device 510 is inserted into groove 515 by twisting the marker and frame 502 relative to one another. As the marker is twisted relative to the frame, retainer device 510 is biased into groove 515 and the physician obtains a tactile sensation that the marker is held in place. To free the marker to again slide relative to the frame, the physician once again twists the marker until retainer device 510 has slid out of groove 515 and is positioned against the cylindrical bore as shown at reference numeral 523 in FIG. 6B, which is a sectional view of marker 508 taken along line 6B-6B of FIG. 6. One of ordinary skill in the art would recognize numerous other mechanical means to allow the markers to slide relative to the frame and be held into place along the frame as desired.

Other means for moving the markers of the array relative to the frame are also possible. For example, referring now to FIG. 7A, tracking array 600 includes frame 602 that has two movable arm members 630, 632 having markers 606, 608 attached at one end. Frame 602 also includes short arms 634, 636 which, through the assistance of a series of hinge members 640, 642, 644, 646 and outer sleeve member 622, allow arm members 630, 632 to pivot relative to one another. In addition to secured markers 606, 608, frame 602 also includes marker 604, which is attached to outer sleeve member 622 and may be moved from a first position (i.e., retainer 616b) to a second position (i.e., retainer 616a) as the sleeve member is moved relative to the frame.

Figure 7A:
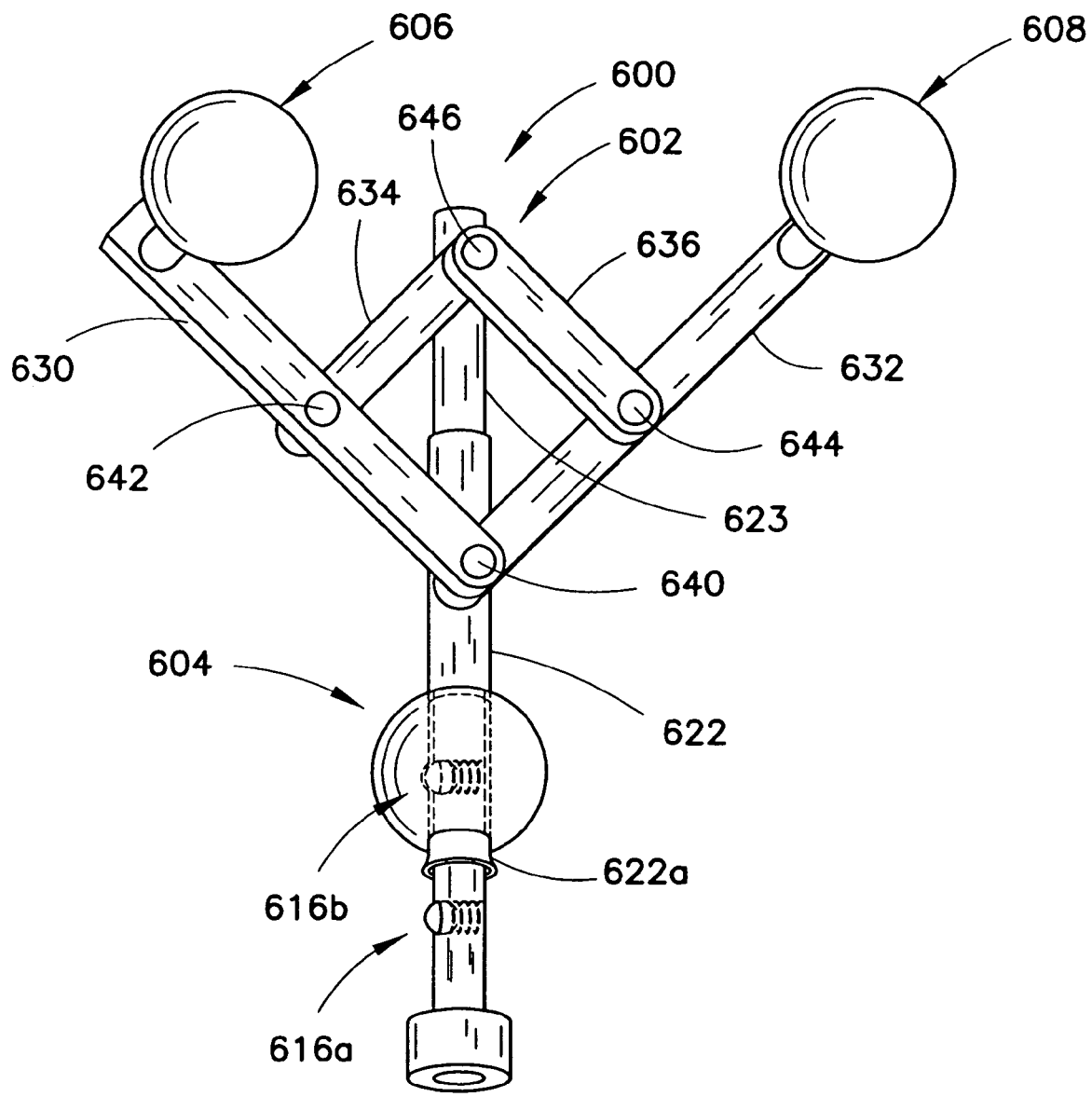
FIGS. 7A-7B are perspective views illustrating an example of an alternative embodiment of an exemplary tracking array having its markers moved in accordance with the present teachings.
Figure 7B:
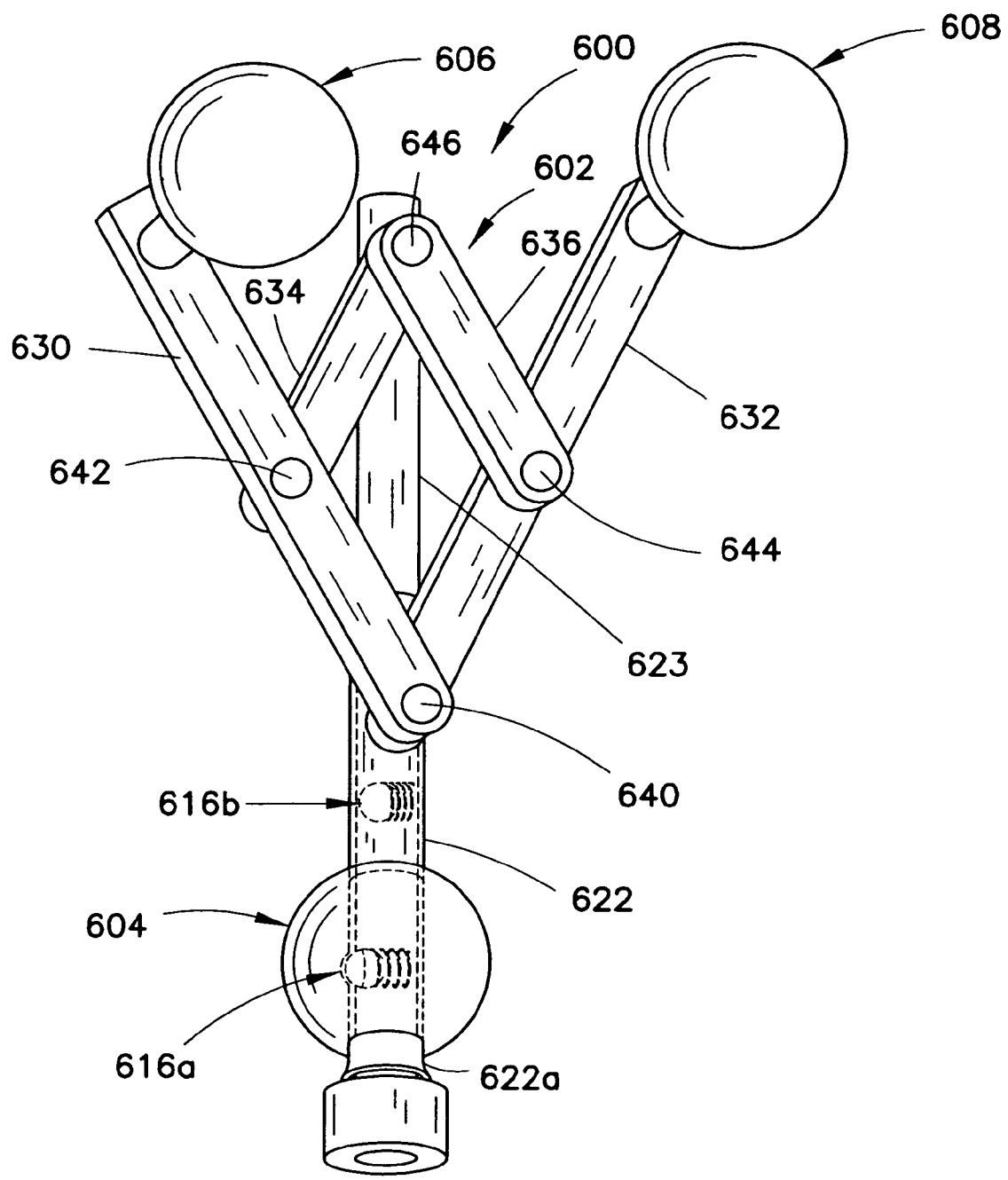

Outer sleeve member 622 defines a central bore that slidably receives shaft 623 as marker 604 is moved between retainers 616b and 616a. Sleeve member 622 has a flared portion 622a at one end so that the retaining device protruding from shaft 623 at the location of retainer 616a is able to enter the central bore of the shaft without difficulty as marker 604 is repositioned along the frame. When marker 604 is moved from retainer 616b to the location of retainer 616a, outer sleeve member 622 (through the assistance of hinge members 640, 642, 644, 646) causes movable arm members 630, 632 to pivot markers 606, 608 inwardly towards each other, as seen in FIG. 7B. Alternatively, by moving marker 604 from the location of retainer 616a to the location of retainer 616b, outer sleeve member 622 causes movable arm members 630, 632 to pivot markers 606, 608 outwardly away from each other, as seen in FIG. 7A.

Figure 8A:
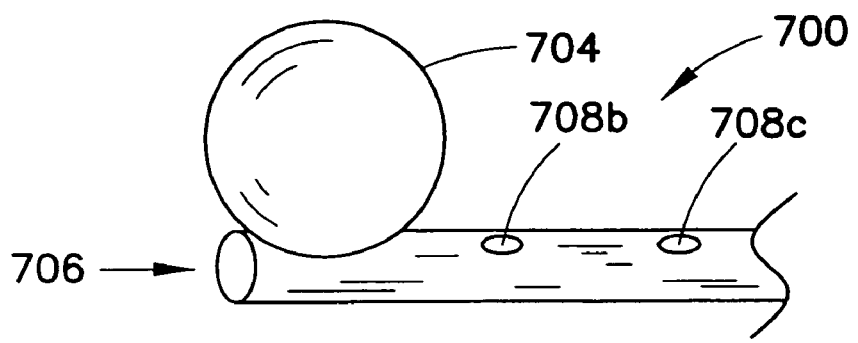
FIGS. 8A-8C are fragmentary perspective views illustrating an example of an exemplary tracking array marker being moved from a first position to a second position in accordance with the present teachings.
Figure 8B:
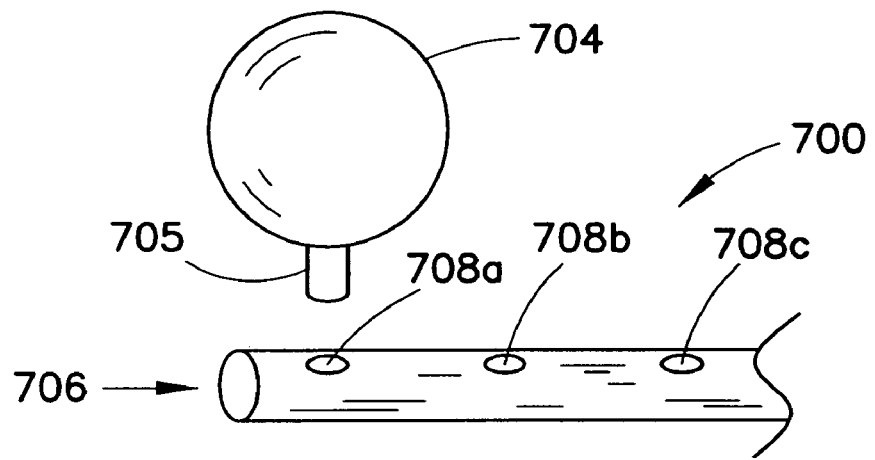
Figure 8C:
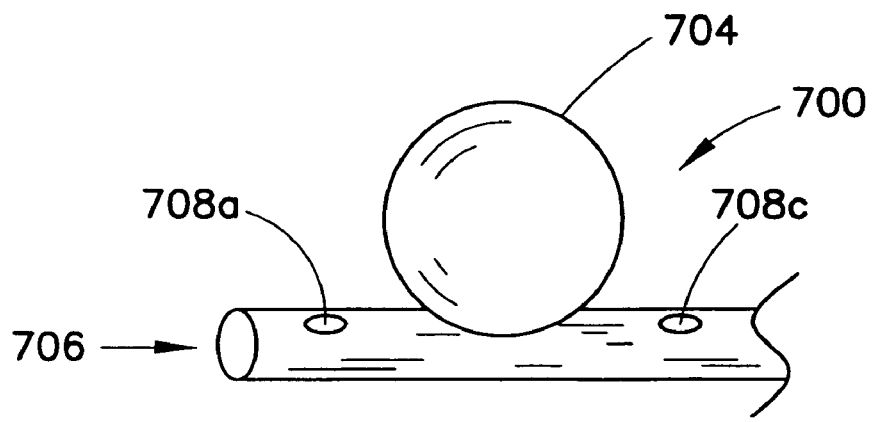

Referring now to FIGS. 8A-8C, an exemplary alternative embodiment depicting the repositioning of a marker on tracking array 700 is shown. Arm member 706 has three retaining holes 708a, 708b, 708c for attaching marker 704 to the arm member. Marker 704 may be physically removed or detached from arm member 706 and then repositioned at any of the retaining hole positions (708a, 708b, 708c) along the arm member. As can be seen in FIG. 8B, marker 704 has an attachment member or retaining peg 705 that may be inserted into any of retaining holes 708a, 708b, 708c to attach marker 704 to arm member 706 at a desired location. For instance, marker 704 moves from retaining hole 708a (FIG. 8A) to hole 708B (FIG. 8C) in this embodiment. While this exemplary illustration describes the releasable attachment of marker 704 to arm member 706 as fitting a retaining peg into a retaining hole, it is envisioned that those skilled in the art may also utilize numerous other attachment configurations. Moreover, in further exemplary embodiments, one or more of the arm members (such as 706) forming the tracking array may be removable from the tracking array and capable of being repositioned. As such, the specific tracking array embodiments described above are not intended to be limiting in nature. Indeed, these teachings contemplate a wide variety of means for moving one or more markers relative to the frame.

Figure 9:
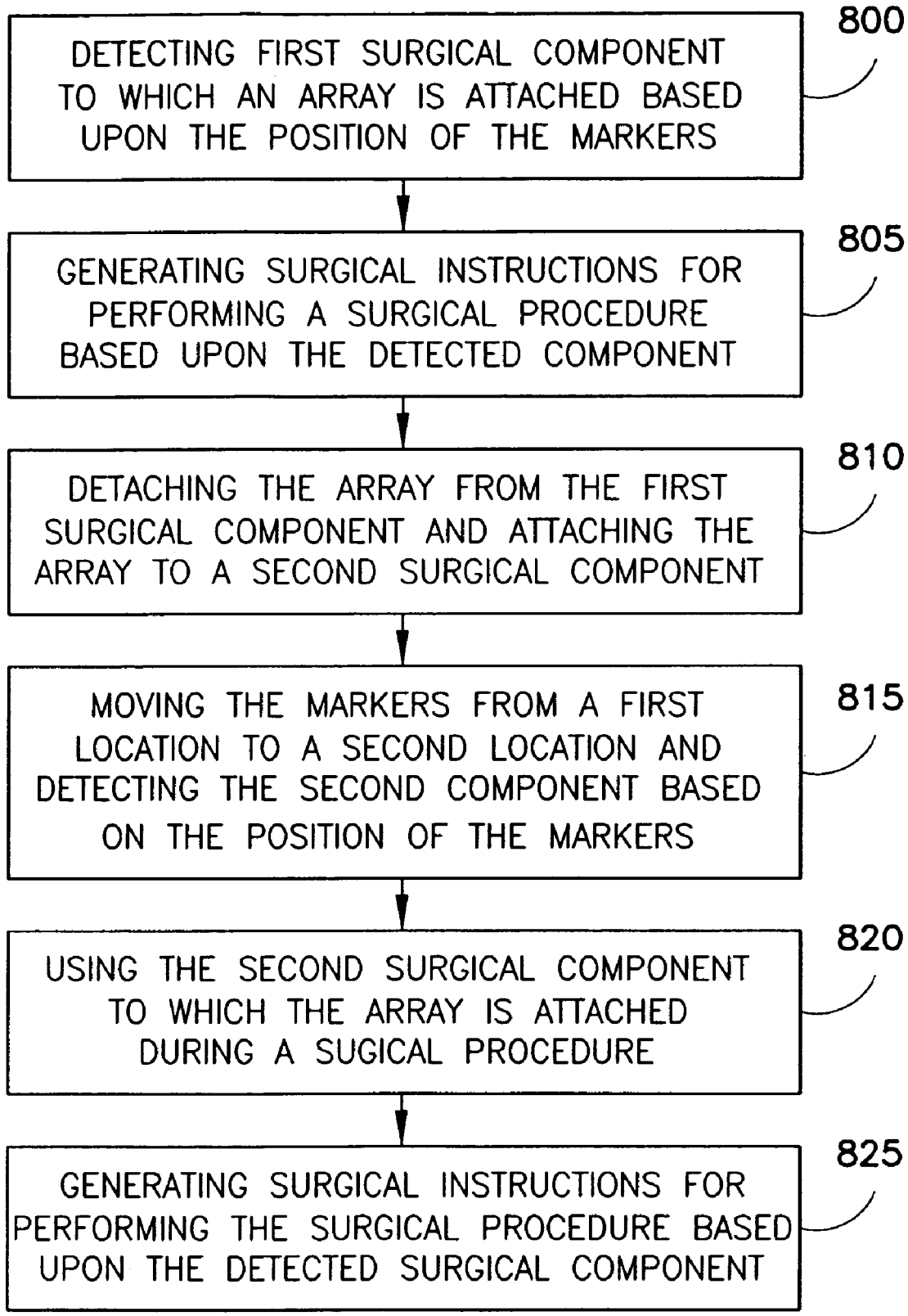
FIG. 9 is a flowchart illustrating an exemplary method incorporating the present teachings.
Figure 10:
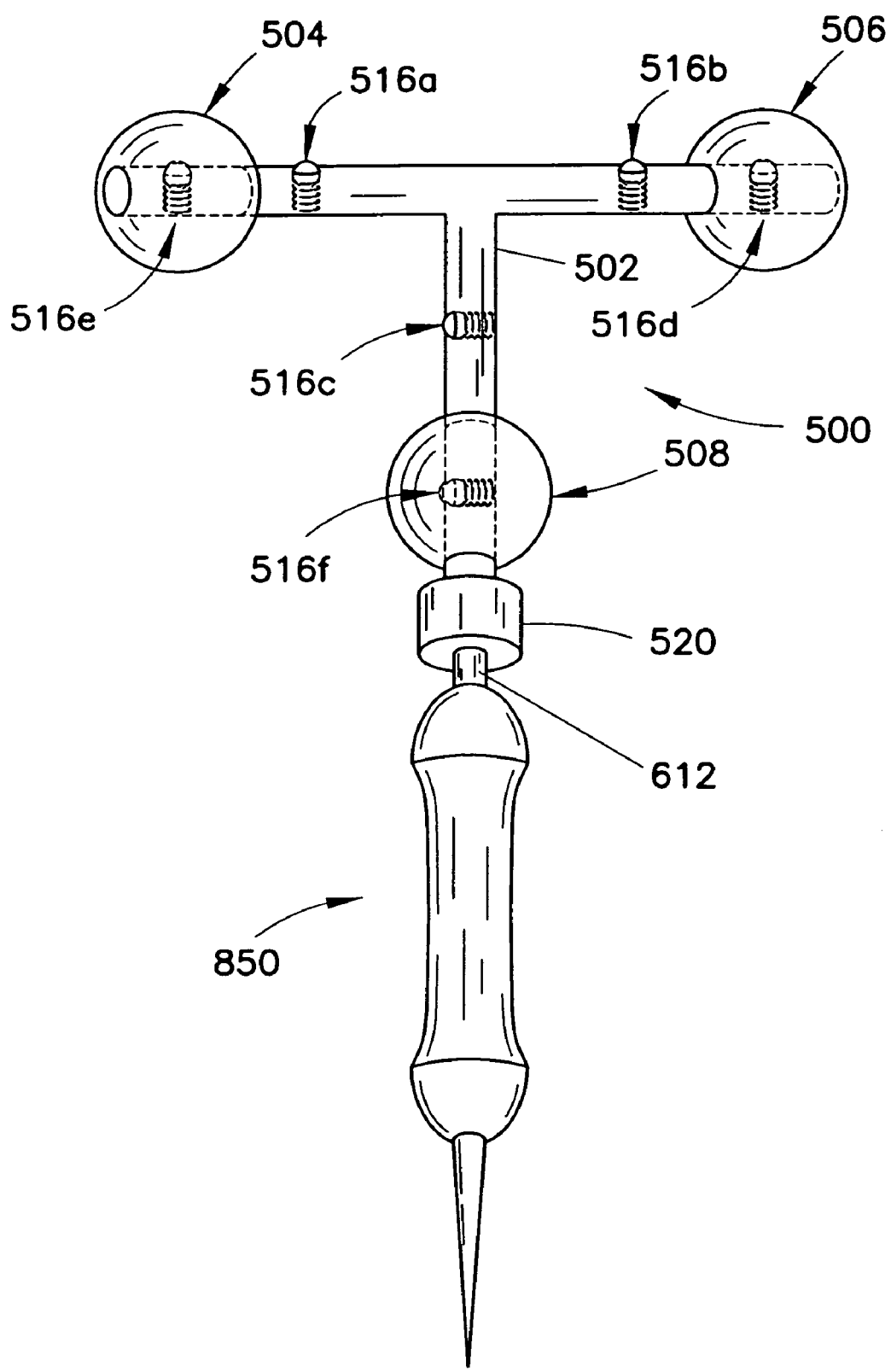
FIG. 10 is a perspective view of an exemplary tracking array in accordance with the present teachings shown attached to a surgical probe instrument.
Figure 11:
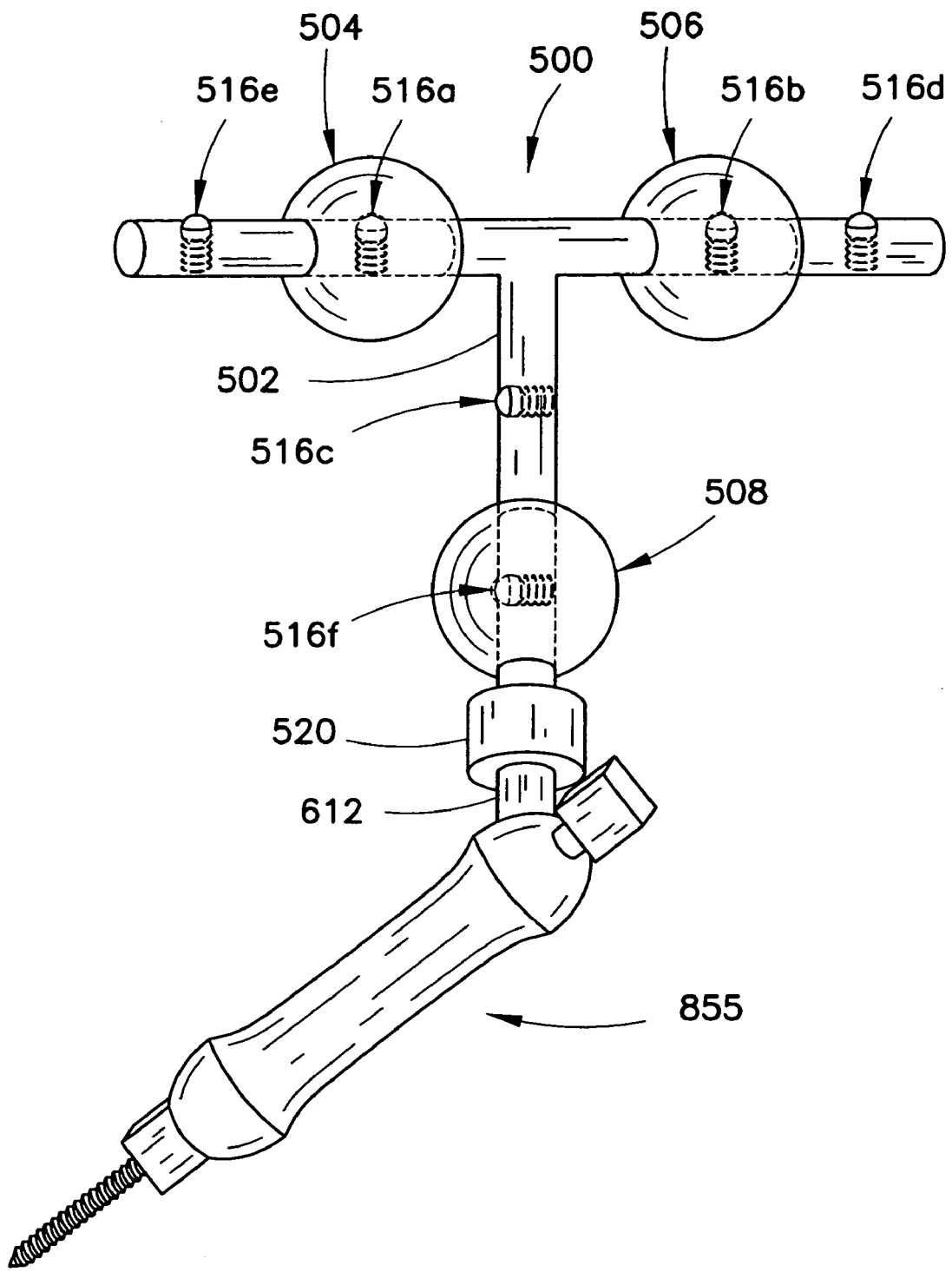
FIG. 11 is a perspective view of an exemplary tracking array in accordance with the present teachings shown attached to a surgical driver device.

An exemplary method of using arrays embodied by the present teachings is described with reference to FIGS. 9-11. In one exemplary embodiment, a method of performing a surgery with a surgical navigation system utilizing an adjustable array is disclosed. According to this exemplary embodiment, and referring to FIG. 9, a surgical navigation tracking system has a camera and computer software detection program that detects and identifies a first surgical component to which an array is attached based upon the position of markers 504, 506, 508 relative to frame 502 (step 800). By recognizing the location of the markers, navigation system 20 generates step-by-step surgical instructions to the physician indicating how to perform the surgical procedure based upon the use of such surgical component (step 805). Navigation system 20 may also advance the surgical procedure to a specific instructional page on the monitor based upon the spatial configuration of the markers.

Once the tracking array is detached from the surgical component, the tracking system detects when a second surgical component is attached to the array by recognizing the new position of markers 504, 506, 508 relative to frame 502 (step 810). More particularly, if a physician moves one or more of markers 504, 506, 508 from a first retainer location to a second retainer location, the tracking system recognizes the new surgical component to which the array is attached based upon the new position of markers 504, 506, 508 relative to frame 502 (step 815). In other words, the physician moves markers 504, 506, 508 from a first position having a first three-dimensional configuration to a second position having a second three-dimensional configuration that is different from the first configuration. As such, the tracking system identifies the change in configuration and recognizes the new surgical component to which the array is attached. The physician then uses the second surgical component and receives any needed surgical instructions useful for performing the surgery in light of the newly detected component (steps 820, 825).

According to this embodiment, navigation system 20 recognizes and identifies a surgical component that is attached to the tracking array based upon the three-dimensional configuration of the markers along the frame. More particularly, since each configuration in which the tracking array can be configured is unique, the navigation system 20 identifies and distinguishes between them. For example, if navigation system 20 determines that the position of marker 504 is at retainer 516*e*, the position of marker 506 is at retainer 516*d* and the position of marker 508 is at retainer 516*f*, then navigation system 20 recognizes that this marker configuration defines the use of a surgical probe instrument, such as surgical probe 850 illustratively depicted in FIG. 10, for instance. Moreover, if navigation system 20 determines that marker 504 is positioned at retainer 516*a*, marker 506 is positioned at retainer 516*b* and marker 508 is positioned at retainer 516*f*, then navigation system 20 recognizes that this marker configuration corresponds to a surgical driver device, such as surgical driver device 855 depicted in FIG. 11.

Figure 12A:
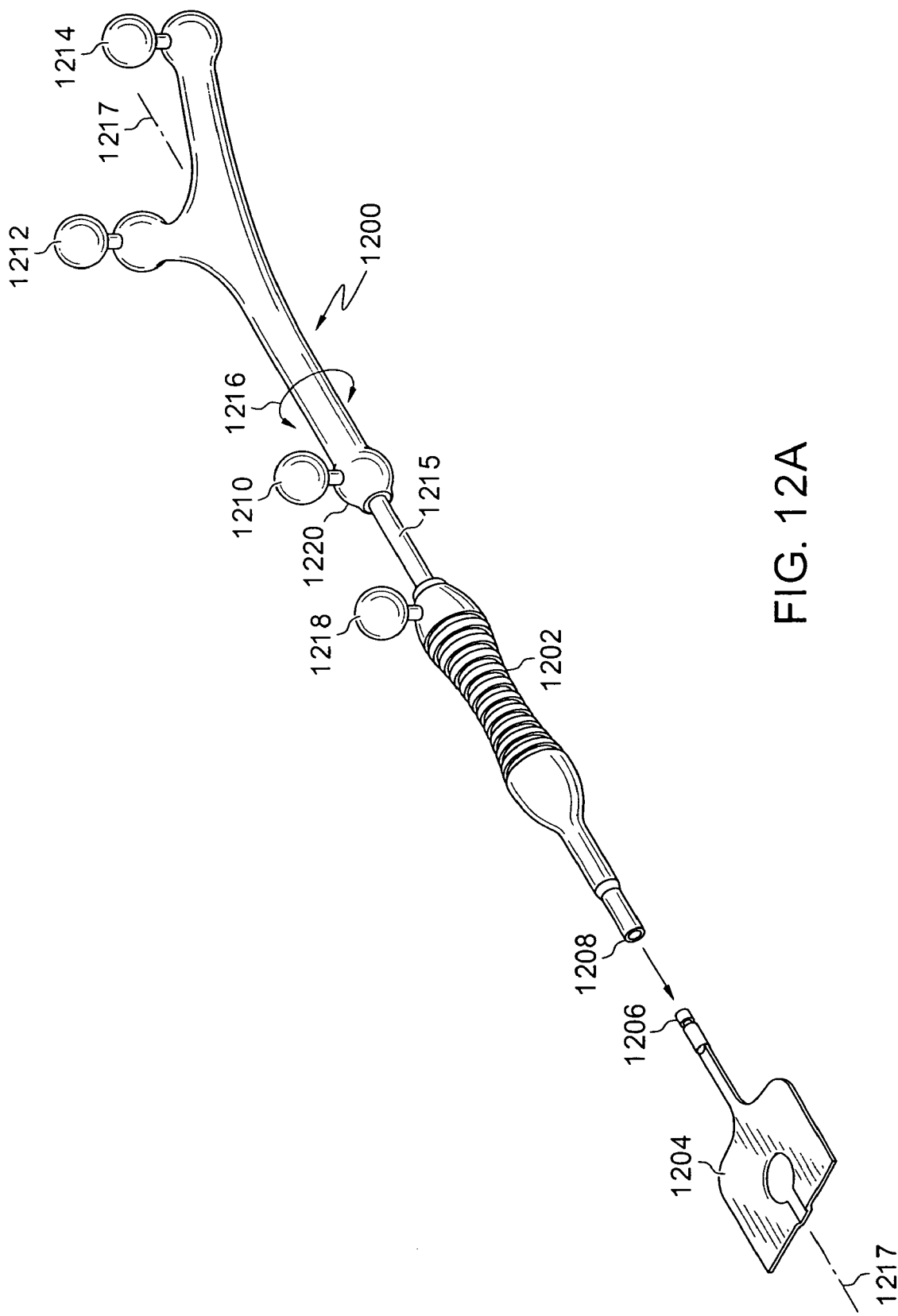
FIG. 12A is a perspective view of an exemplary embodiment of an array and component removably attached to the array.
Figure 12B:
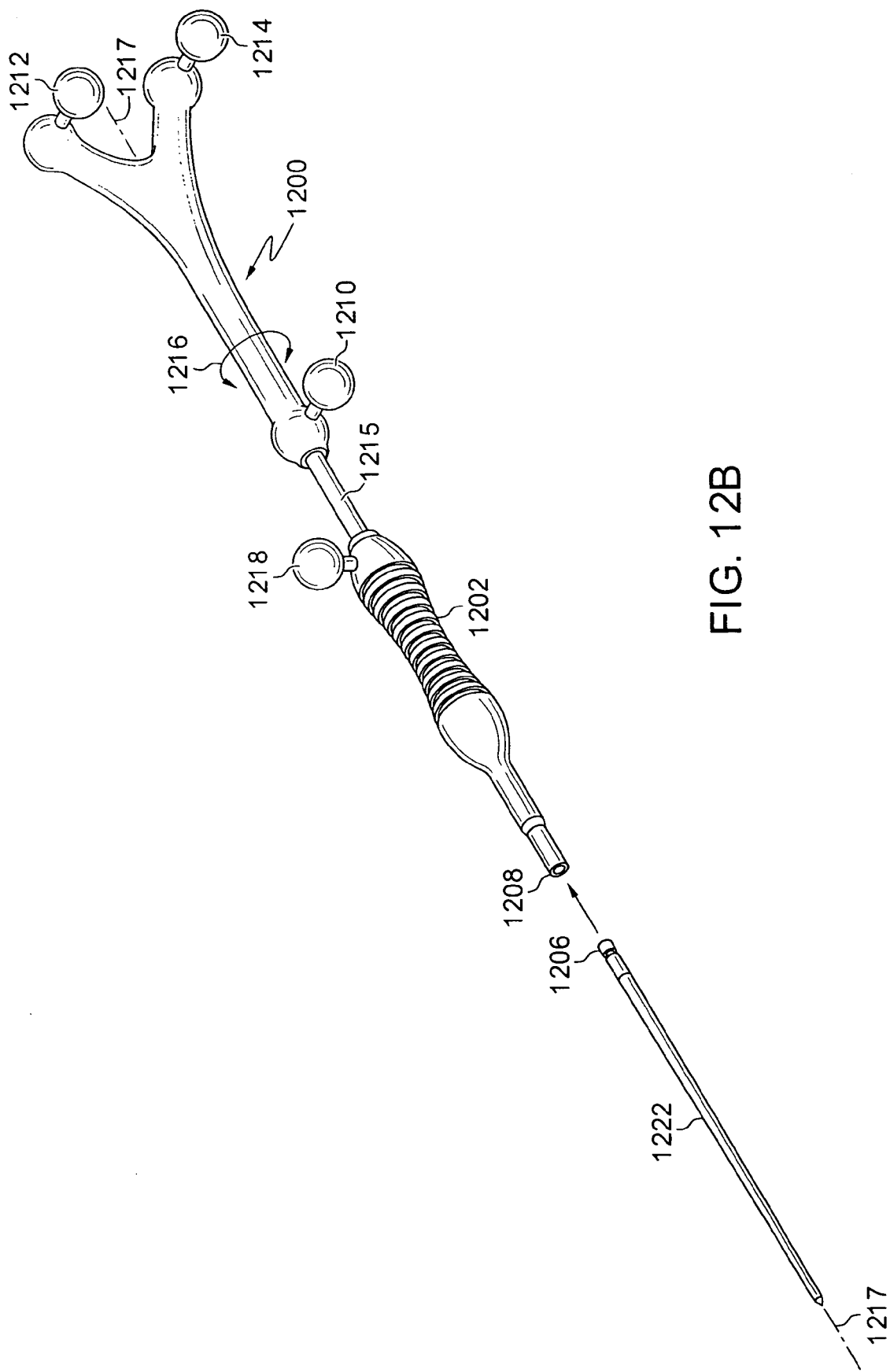
FIG. 12B is a perspective view of the array of FIG. 12A having a different component removably attached to the array.

According to another embodiment shown in FIGS. 12A and 12B, array 1200 for use with a surgical navigation system includes frame 1202 and a surgical component or spatula 1204 that is connectable to frame 1202. Connector 1206 snap fits into receptacle 1208 as shown, such that multiple different components can be interchangeably and removably connected to frame 1202. As shown in FIG. 12A, markers 1210, 1212 and 1214 are attached to the frame by means of connecting bar 1215 and are able to rotate with respect to a longitudinal axis 1217 of frame 1202 in the direction of arrow 1216 as shown. A fourth marker 1218 is fixed to the frame by connecting bar 1220. Markers 1210, 1212, 1214 and 1218 form an array that is detectable by a tracking system used in a surgical navigation system. As shown, markers 1210, 1212 and 1214 are rotatable as a unit with respect to longitudinal axis 1217 of frame 1202. That is, markers 1210, 1212 and 1214 move angularly as a unit relative to the fourth marker 1218 and the longitudinal axis of the frame.

The navigation system can be configured to recognize different rotational or angular geometries as corresponding to different surgical components. For example, as shown in FIG. 12A, the four markers are disposed substantially in the same plane, and the navigation system can be configured to recognize this marker geometry as corresponding to the spatula probe 1204 as shown. Similarly, if the three markers 1210, 1212 and 1214 are rotated 90 degrees from the position shown in FIG. 12A to the position shown in FIG. 12B, the system would recognize the new three dimensional configuration of the array as corresponding to pointer probe component 1222 as shown in FIG. 12B.

Thus, with the embodiment shown in FIGS. 12A and 12B, a probe handle defined by frame 1202 and spheres 1210, 1212, 1214 and 1218 can be reconfigured in several different geometries. Ninety degree increments may be chosen, such that each probe handle with array can be used with four different surgical components. For each component, the probe's array will have a unique geometry that is identifiable by the tracking system. The probe can be configured to interchangeably accept as many different surgical components as there are incremental positions of the handle.

In yet another variation of the embodiment shown in FIGS. 12A and 12B, the probe handle can be configured to rotate freely and the navigation system configured to recognize the infinite number of positions along the full 360 degrees of rotation. At all positions about the entire 360 degree rotation, the navigation system would be configured to recognize the same probe. In this manner, a full range of camera visibility would be created, resulting in a more versatile and functional probe.

Figure 13A:
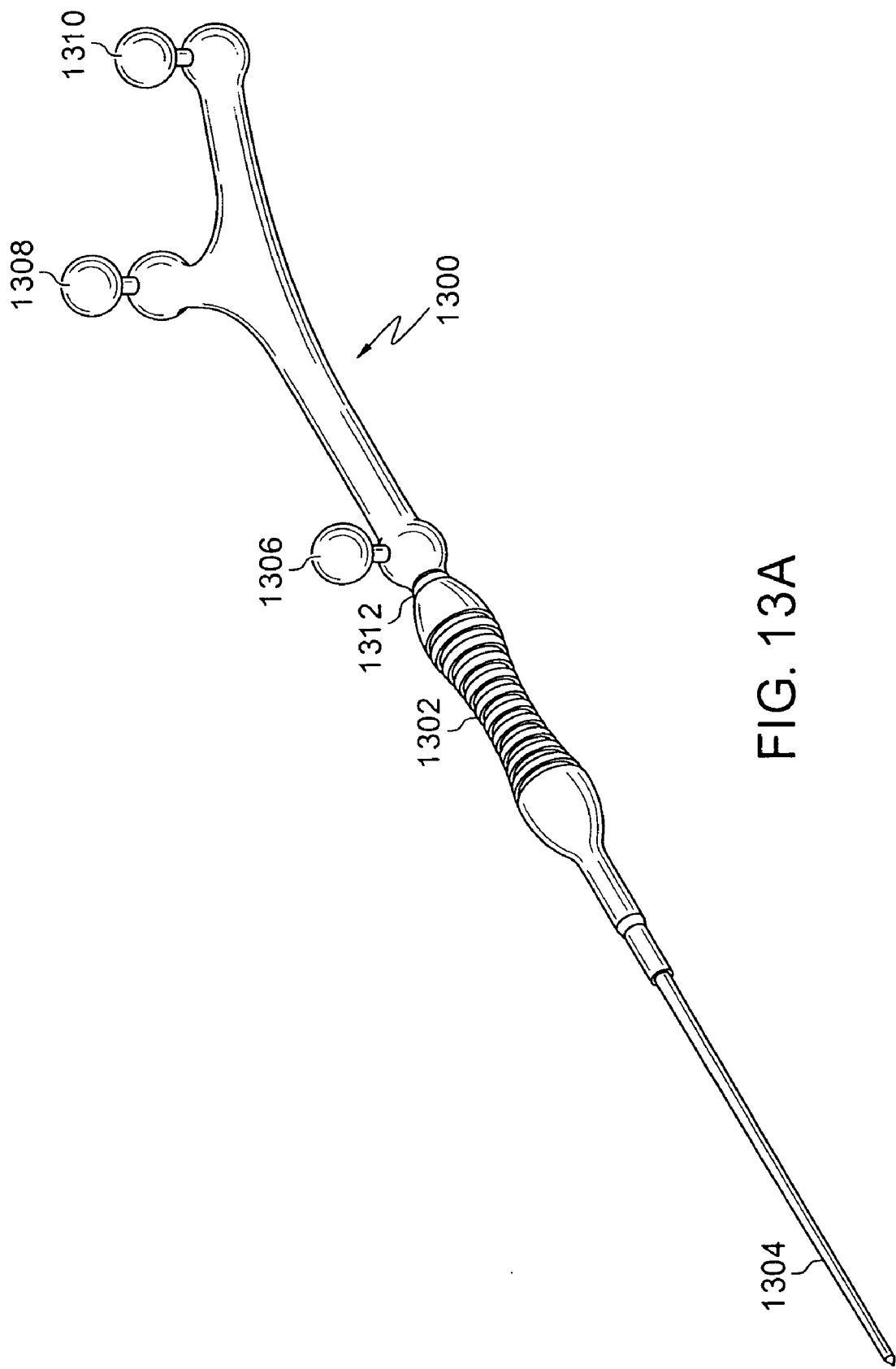
FIG. 13A is a perspective view of an exemplary embodiment of an array and surgical component that is removably attached to the array.
Figure 13B:
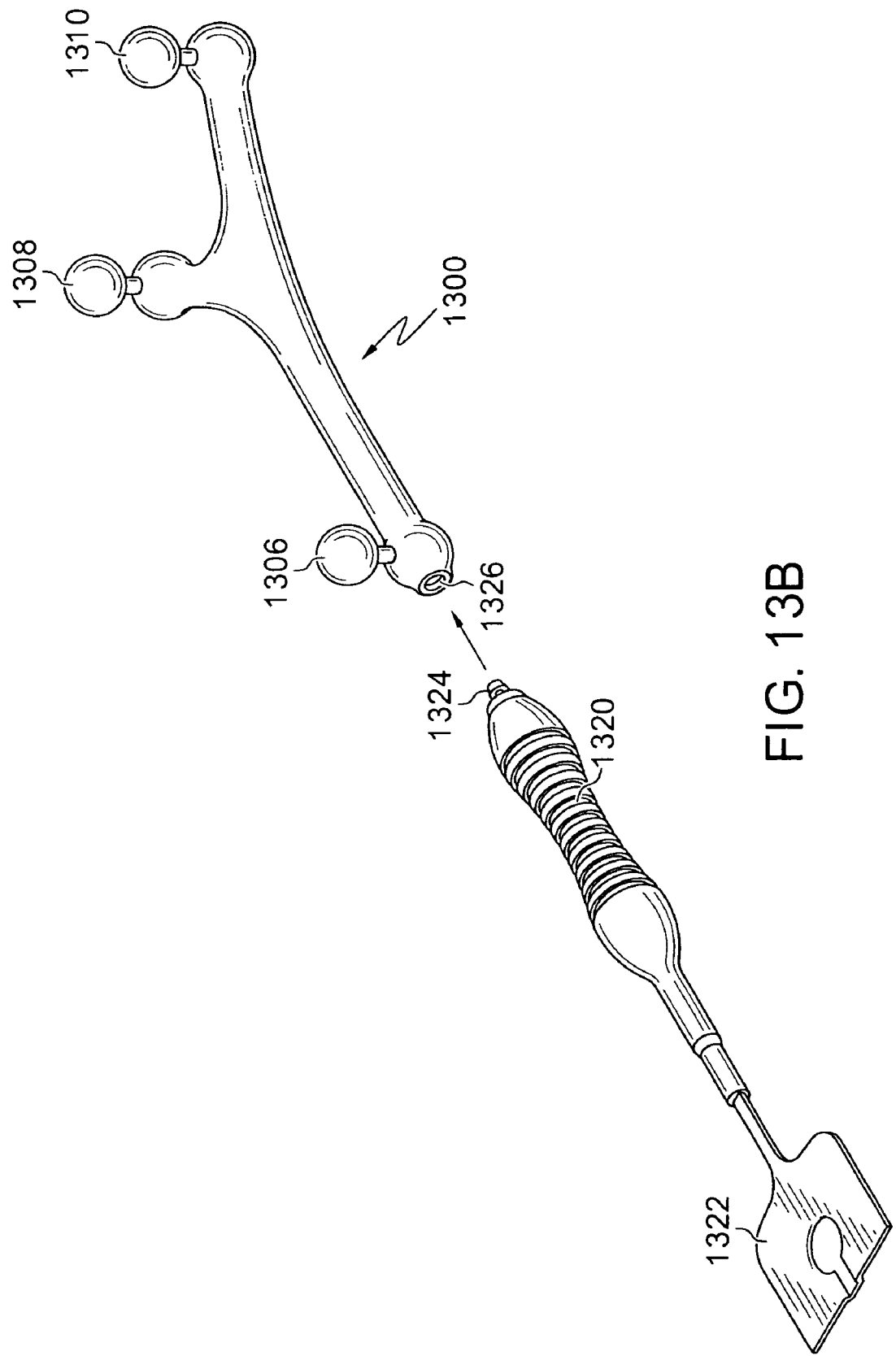
FIG. 13B is a perspective view of the array of FIG. 13A having a different component removably attachable to the array.
Figure 14:
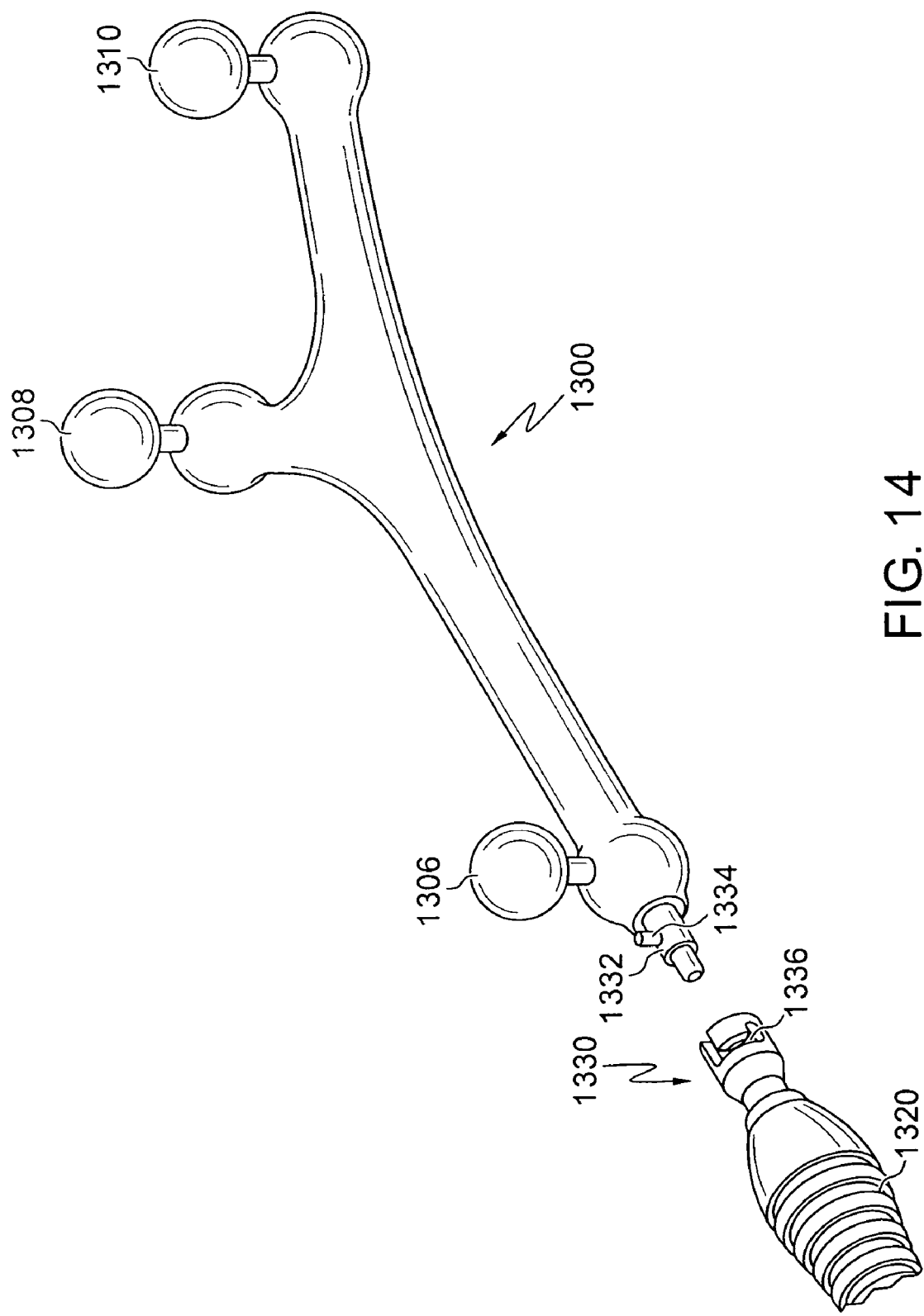
FIG. 14 is a perspective view illustrating a quick disconnect fitting between an array and a surgical component.

The embodiment shown in FIGS. 13A and 13B illustrates an instrument set for use in surgical navigation. Array 1300 is shown in FIG. 13A as attached to a frame or handle 1302 having an extending probe 1304. The array includes three markers 1306, 1308 and 1310. The handle 1302 is detachably connected to the array at connection point 1312. As shown in FIG. 13B, array 1300 can be removed and then re-attached to a different probe handle 1320 having a spatula end 1322 extending from handle 1320. A conventional quick connect fitting 1324 snap fits into receptacle 1326. Alternatively, as shown in FIG. 14, an alternate quick connect can be employed. This quick connect includes male end 1332, which inserts into female end 1330 and is then twisted such that peg 1334 slides through and locks into slot 1336.

As can be appreciated with respect to FIGS. 13A and 13B, a versatile instrument set for use in surgical navigation can be created. For example, the instrument set includes several arrays with different geometries and passive sphere placements. These different sizes and sphere layouts of the arrays are recognizable and distinguishable by the navigation system. In most surgical applications, however, more arrays are provided than are needed. Thus, if more probe configurations were desired, they can be provided in the form of a tip or handle instead of an entire "probe array." This approach could reduce instrument costs by not having to create a special mold for additional probe bodies. Instead, the additional probes would use the arrays of the instrument set that are not being used during the procedure.

The navigation system would need to be programmed to mix and match probe components and arrays, and during use the identity of the particular array and probe body would need to be inputted into the navigation system. The surgeon's tool belt could be configured with smaller probe heads or handles instead of larger and bulkier probe arrays. Of course, one of skill in the art would recognize numerous other possibilities obtainable with the modular features of an instrument set as illustrated above.

It should now be appreciated that a surgical system can be created in accordance with these teachings that includes a computer having surgical navigation utilities software, as described above, and a tracking system coupled to the computer. One or several arrays having a unique marker geometry that is identifiable by the tracking system are provided. Several different surgical components such as the pointer probe tip 1222 and spatula tip 1204 are provided and are removably and interchangeably connectable to the array or array handle. The software is programmed to accept the identity of each surgical component as an input, such that the surgical navigation system can recognize and track any one of the plurality of surgical components that is connected to the array. This modular capability reduces overall costs by reducing the number of components in a surgical navigation kit and at the same time increases flexibility.

While exemplary embodiments incorporating the principles of the present teachings have been disclosed hereinabove, the present teachings are not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An array for use with a surgical navigation system, comprising:
    a frame having a plurality of retainers configured to a marker thereto; and
    first, second and third markers attached to the frame, the first, second and third markers defining a first three-dimensional configuration of the array that is detectable by a tracking system used in a surgical navigation system;
    wherein the first marker is movable relative to the frame from a first retainer to a second unoccupied retainer to define a second three-dimensional configuration of the array, the second three-dimensional configuration being different from the first three-dimensional configuration.

2. The array of claim 1, wherein the first marker is slidable on the frame between a first position and a second position.

3. The array of claim 1, further comprising a coupling member disposed at one end of the frame and adapted to releasably and interchangeably attach the array to at least two different surgical components to distinguish between the at least two different surgical components through detection of at least one of the first, second and third markers.

4. The array of claim 1, wherein the frame comprises a movable arm member having the first marker attached thereto, wherein the movable arm member and the first marker move relative to the frame.

5. The array of claim 1, wherein the first marker is detachable from the frame at a first position and reattachable to the frame at a second position.

6. A method of performing a surgery using surgical navigation, comprising:
    (a) providing a tracking system and an array having a frame having a plurality of retainers with first, second and third markers attached thereto, the array being identified and tracked by the tracking system;
    (b) using a first surgical component to which the array is attached during the surgery while tracking the first surgical component with the tracking system;
    (c) detaching the array from the first surgical component and reattaching the array to a second surgical component;
    (d) moving the position of the first marker from a first position to a second position relative to the frame, wherein the tracking system identifies the second surgical component to which the array is attached; and
    (e) using the second surgical component to which the array is attached during the surgery while tracking the second surgical component with the tracking system.

7. The method of claim 6, wherein step (d) comprises sliding the first marker along the frame from the first position to the second position.

8. The method of claim 6, wherein step (d) comprises moving a movable arm member having the first marker attached thereto, wherein the first marker moves from the first position to the second position.

9. The method of claim 8, wherein step (d) comprises detaching the first marker from the frame at the first position and reattaching the first marker to the frame at the second position.

10. A surgical navigation system, comprising:
    a computer having surgical navigation utilities software;
    a tracking system coupled to the computer;
    an array having a frame with a plurality of retainers configured to couple a marker thereto and a marker geometry that is identifiable by the tracking system, the marker geometry being defined by first, second and third markers that are interchangeable between at least two different three-dimensional configurations by moving the first marker relative to the frame from a first retainer to a second unoccupied retainer, each three-dimensional configuration being identifiable and distinguishable by the tracking system; and
    a plurality of different surgical components that are removably and interchangeably connectable to the array;
    the software programmed to accept the identity of each surgical component as an input, wherein the surgical navigation system is configured to recognize and track any one of the plurality of surgical components that is connected to the array.

11. The surgical navigation system of claim 10, further comprising a coupling member disposed at one end and adapted to releasably and interchangeably attach the array to the plurality of different surgical components to distinguish between the surgical components through detection of at least one of the first, second and third markers.

* * * * *